United States Patent
Ishiduka et al.

(10) Patent No.: US 6,323,330 B1
(45) Date of Patent: Nov. 27, 2001

(54) PROTEIN C16 AND C16N OR GENES ENCODING THE SAME

(75) Inventors: Yasuyuki Ishiduka, Osaka; Reiko Mochizuki, Ichikawa, both of (JP)

(73) Assignee: Sumitomo Pharmaceuticals Company, Limited, Osaka ( * ) Notice: Subject to any disclaimer, the term of this patent is extended or adjusted under 35 U.S.C. 154(b) by 0 days.

(21) Appl. No.: 09/171,710

(22) PCT Filed: Apr. 23, 1997

(86) PCT No.: PCT/JP97/01391

§ 371 Date: Oct. 23, 1998

§ 102(e) Date: Oct. 23, 1998

(87) PCT Pub. No.: WO97/40150

PCT Pub. Date: Oct. 30, 1997

(30) Foreign Application Priority Data

Apr. 23, 1996 (JP) .................................... 8-127954
Feb. 10, 1997 (JP) .................................... 9-041562

(51) Int. Cl.[7] .......................... C07H 21/02; C07H 21/04; C12N 15/63; C12N 15/85; C12N 15/86; C12N 21/00

(52) U.S. Cl. ..................... 536/23.1; 435/320.1; 435/325; 435/70.1; 536/23.5

(58) Field of Search ................................ 536/23.1, 23.5; 435/320.1, 325, 70.1; 800/8, 2; 514/44

(56) References Cited

U.S. PATENT DOCUMENTS 5,650,550 * 7/1997 Korach et al. ........................... 800/2

OTHER PUBLICATIONS

Adams et al 1993. Genbank accession No. Q61345, WO9316178.*
Cameron ER. Molecular Biotechnology 7:253–265, 1997.*
Mullins JJ et al. Hypertension 22:630–633 1993.*
Hammer RE et al. Cell 63:1099–1112. 1990.*
Seidel GE. J. Anim. Sci. 71(Suppl. 3):26–33, 1993.*
Ishiduka et al 1999 Genbank accession No. AB017609, AB017608.*
J.A. Parsons, Peptide Hormones, "Characteristics of the amino acids as components of a peptide hormone sequence," Natl. Inst. for Medical Research, Univ. Park Press, Jun. 1976, pp. 1–7.*
Short protocols in molecular biology, "Screening of recombinant DNA libraries," 3rd. Edition, published by John Wiley & Sons, Inc., p6–1/6–4.*
Nature, vol. 355, No. 6361, (1992), J. Craig Venter et al; "Sequence identification of 2,375 human brain genes.", see p. 632–634.
Nature Genet., vol. 4, (1993), J. Craig Venter et al., Rapid cDNA Sequencing (expressed sequence tags) from a directionally cloned human infant brain cDNA library.:, see p. 373–380.
Science, vol. 252, (1991), J. Craig Venter et al., "Complementary DNA Sequencing: Expressed Sequence Tags and Human Genome Project.", see p. 1651–1656.
The Journal of Biological chemistry, vol. 268, No. 4 (1993), K. Naruo et al.; "Novel Secretory Heparin–binding Factors from Human Glioma Cells (Glia–activating Factors), Involved in Glial Cell Growth.", see p. 2857–2864.

* cited by examiner

Primary Examiner—Scott D. Priebe
Assistant Examiner—Ram R. Shukla
(74) Attorney, Agent, or Firm—Birch, Stewart, Kolasch & Birch, LLP

(57) ABSTRACT

Novel proteins C16 and C16N or genes encoding the same; proteins analogous to these novel proteins; partial peptides; antibodies; transgenic animals; a method for screening inhibitors by using these novel proteins; inhibitors obtained by the above screening method; etc. are provided. The novel proteins C16 and C16N or the proteins analogous thereto have the activities of inducing cells to become capable of resorbing hydroxyapatite, maintaining the survival of neurons, inhibiting the proliferation of osteoblasts, and/or promoting the expression of type I collagen in osteoblasts. Thus, the above proteins are applicable to the treatment of various diseases which are curable through expression of these functions.

5 Claims, 13 Drawing Sheets

*) 1α,25(OH)₂D₃/dexamethasone

For ST2 cells, analysis was done in the presence of VD$_3$

SEQUENCE LISTING

<160> NUMBER OF SEQ ID NOS: 14

<210> SEQ ID NO 1
<211> LENGTH: 2911
<212> TYPE: DNA
<213> ORGANISM: Mus sp.

<400> SEQUENCE: 1

```
ccgacgtagg atctttgatg ccgttgggtt cacctttccc aaccgactcc tgaccactaa    60
ggaggcacct gatggctgcc ctgaccacgt tctccgggcc ctgggcgtgg ccctgctggc   120
ctgtttctgc agcgaccctg aactagccag ccatcccag gtcctgaaca agatccccat   180
ccttagcaca ttccttacag cccgggggga ccctgatgat gctgcccgcc gctccatgat   240
cgatgacacc taccagtgcc tgacagctgt tgcgggcaca ccccgagggc cccggcacct   300
cattgctggt ggcaccgtgt ctgccctgtg ccaggcgtac ctggggcatg gctacggctt   360
tgaccaggct ctggcactct tggtgggct gctggctgct gcagagacac agtgctggaa   420
ggaggcggag cccgacctgc tggctgtgtt gcgaggcctc agtgaggatt tccaaagagc   480
cgaagatgcc agcaagtttg agctctgcca gctgctgccc cttttttctgc ccccaacaac   540 tgtgcccct gaatgccacc gagatctgca ggctgggctg gcacgaatcc taggaagcaa   600
gttgagctcc tggcagcgca accctgcact gaagctggca gcccgcctgg ctcatgcctg   660
cggctccgac tggatcccag tgggcagctc tgggagcaag tttctggccc tgctcgtgaa   720
tctagcgtgc gtggaggtac ggctggctct cgaggagaca ggcacagagg tgaaagaaga   780
cgtggtaaca gcctgctatg cccttatgga attggggatc caggagtgca cccgctgtga   840
gcagtccctg cttaaggagc cacagaaggt tcagctcgtg agcattatga aagaggccat   900
tggcgctgtc atccactacc tgctgcaggt ggggccagag aagcagaaag agcctttgt   960 gtttgcctcg tgcggatcct gggtgcctgg ctggcggagg agacctcatc cctgcgtaag  1020
gaggtgtgcc aactgctgcc cttccttgtc cgatatgcca agacactcta tgaggaggct  1080
gaggaggcca gtgacatttc gcagcaggtg gccaacttgg ccatctctcc tactacaccg  1140
ggccatgata cctcagtgct gccagacagc gtggagatcg gccttcagac ctgttgccat  1200
atcttcctca acctggtggt caccgctcca gggctgatca aacgcgatgc ctgcttcaca  1260
```

```
tctcttatga acaccctgat gacgtcactg ccctcactag tgcagcaaca agggagactg   1320
cttctagctg ccaacgtggc cactttgggg ctcctaatgg cccggctcct tagcacctct   1380
ccagctctcc aaggaacccc agcctcccga ggtttcttcg cagctgccat cctctttctg   1440
tcacagtccc atgtggcacg agccacccct ggctctgacc aggcagtgtt ggccctgtcc   1500
cctgactatg aaggcatctg gctgacttg caagagctct ggttcctggg catgcaggcc   1560
ttcacgggtt gtgtgccgct gctgccctgg ctggcccctg ccgccctgcg ctcccgctgg   1620
ccacaggagc tgctacaact gctaggtagt gtaagcccca actccgtcaa gcctgagatg   1680
gtggctgcct accagggcgt gctggtggaa ttggcacggg ctaaccggct atgccgggag   1740
gccatgaggc tgcaggcggg tgaagaaacg ccagccatt accgaatggc tgctttggag   1800
cagtgcctgt cagagccctg aggggcatcc agtgggtaca gacccaggcg ggcagcgagg   1860
gaaggaggga ggaggcatct tccctgaagc ccccaaactg gaccccttct tcagaccccc   1920
acaaacaccc cagctttctg gcttttctga gggctagggc atggtgccca cctctcaagt   1980
ataagaaact gcatcctgcc tccagccccc ttggggcagg gattggcttg aacagaggt   2040 tggccccgcc aggccgggga aggttggaga agccccagg aggagggcaa ctaagtgtca   2100
ttatacccag tgtctggctc cctgatagga gggaggtccc agggtaggag cgggctggca   2160
ggcgctgact gcctcagccc atgtgccctg ccggccaggc cgtggcctcc caaggctgt   2220 ggtgcccctt ctggctcccc taggtcaggt ccgcgccctt taaattggcc gcttggcttt   2280
tgcctttggt cctcttggac agagagcagg ctcaggccat tgacatcaca gttcttcctt   2340
ttaactctag tgacccgggg tccgagttgc ccctatgctt ccagggcaat ttggagcaga   2400
cagaccagtg gggggtgggg aacctccttc cacctgcgct tccttgaggg gaccagagag   2460
cccttggtcc caggtctctt gagcttttgt gtcatgttgc agcagagtga agatgggggg   2520 ttggggggtta tttattttgc ttgtccttat ccctgcttgg acacctgagc atcagatccc   2580
tgtgcccctg gtgccatctg gcctgctgga gccaggaaca agaggtcacc ccaccctaga   2640
atccgcatgt tttccctgtg attgcactcc actgccaccg tggtgcctgg cttcagctcc   2700 cctccccaa tccctgctaa gcctctactc tgcagggaga cgcgactggc ggctccagca   2760
ggaactacct ttctgaaccc gcggagaccc gcataagcct gaccccttgc ttcctccccg   2820 cccccagtg cgttctgtga tcgccaagtt caaagctgtg cacatgtgga cactcaataa   2880
atgtttattg gtgaaaaaaa aaaaaaaaa a                                   2911
```

<210> SEQ ID NO 2
<211> LENGTH: 333
<212> TYPE: PRT
<213> ORGANISM: Mus sp.

<400> SEQUENCE: 2

```
Met Ile Asp Asp Thr Tyr Gln Cys Leu Thr Ala Val Ala Gly Thr Pro
 1               5                  10                  15

Arg Gly Pro Arg His Leu Ile Ala Gly Gly Thr Val Ser Ala Leu Cys
            20                  25                  30

Gln Ala Tyr Leu Gly His Gly Tyr Gly Phe Asp Gln Ala Leu Ala Leu
        35                  40                  45

Leu Val Gly Leu Leu Ala Ala Ala Glu Thr Gln Cys Trp Lys Glu Ala
    50                  55                  60

Glu Pro Asp Leu Leu Ala Val Leu Arg Gly Leu Ser Glu Asp Phe Gln
65                  70                  75                  80
```

-continued

```
Arg Ala Glu Asp Ala Ser Lys Phe Glu Leu Cys Gln Leu Leu Pro Leu
                 85                  90                  95
Phe Leu Pro Pro Thr Thr Val Pro Pro Glu Cys His Arg Asp Leu Gln
            100                 105                 110
Ala Gly Leu Ala Arg Ile Leu Gly Ser Lys Leu Ser Ser Trp Gln Arg
        115                 120                 125
Asn Pro Ala Leu Lys Leu Ala Ala Arg Leu Ala His Ala Cys Gly Ser
    130                 135                 140
Asp Trp Ile Pro Val Gly Ser Ser Gly Ser Lys Phe Leu Ala Leu Leu
145                 150                 155                 160
Val Asn Leu Ala Cys Val Glu Val Arg Leu Ala Leu Glu Glu Thr Gly
                165                 170                 175
Thr Glu Val Lys Glu Asp Val Val Thr Ala Cys Tyr Ala Leu Met Glu
            180                 185                 190
Leu Gly Ile Gln Glu Cys Thr Arg Cys Glu Gln Ser Leu Leu Lys Glu
        195                 200                 205
Pro Gln Lys Val Gln Leu Val Ser Ile Met Lys Glu Ala Ile Gly Ala
    210                 215                 220
Val Ile His Tyr Leu Leu Gln Val Gly Pro Glu Lys Gln Lys Glu Pro
225                 230                 235                 240
Phe Val Phe Ala Ser Cys Gly Ser Trp Val Pro Gly Trp Arg Arg Arg
                245                 250                 255
Pro His Pro Cys Val Arg Arg Cys Ala Asn Cys Cys Pro Ser Leu Ser
            260                 265                 270
Asp Met Pro Arg His Ser Met Arg Arg Leu Arg Arg Pro Val Thr Phe
        275                 280                 285
Arg Ser Arg Trp Pro Thr Trp Pro Ser Leu Leu Leu His Arg Ala Met
    290                 295                 300
Ile Pro Gln Cys Cys Gln Thr Ala Trp Arg Ser Ala Phe Arg Pro Val
305                 310                 315                 320
Ala Ile Ser Ser Ser Thr Trp Trp Ser Pro Leu Gln Gly
                325                 330
```

<210> SEQ ID NO 3
<211> LENGTH: 3065
<212> TYPE: DNA
<213> ORGANISM: Mus sp.

<400> SEQUENCE: 3

```
ccgacgtagg atctttgatg ccgttgggtt cacctttccc aaccgactcc tgaccactaa      60
ggaggcacct gatggctgcc ctgaccacgt tctccgggcc ctgggcgtgg ccctgctggc     120
ctgtttctgc agcgaccctg aactagccag ccatcccag gtcctgaaca agatccccat     180
ccttagcaca ttccttacag cccgggggga ccctgatgat gctgcccgcc gctccatgat     240
cgatgacacc taccagtgcc tgacagctgt tgcgggcaca cccgagggc cccggcacct     300
cattgctggt ggcaccgtgt ctgccctgtg ccaggcgtac ctggggcatg ctacggctt     360
tgaccaggct ctggcactct tggtggggct gctggctgct gcagagacac agtgctggaa     420
ggaggcggag cccgacctgc tggctgtgtt gcgaggcctc agtgaggatt ccaaagagc     480
cgaagatgcc agcaagtttg agctctgcca gctgctgccc cttttctgc ccccaacaac     540
tgtgcccct gaatgccacc gagatctgca ggctgggctg gcacgaatcc taggaagcaa     600
gttgagctcc tggcagcgca accctgcact gaagctggca gccgcctgg ctcatgcctg     660
cggctccgac tggatcccag tgggcagctc tgggagcaag tttctggccc tgctcgtgaa     720
```

```
tctggcgtgc gtggaggtac ggctggctct cgaggagaca ggcacagagg tgaaagaaga    780
cgtggtaaca gcctgctatg cccttatgga attggggatc caggagtgca cccgctgtga    840
gcagtccctg cttaaggagc cacagaaggt tcagctcgtg agcattatga aagaggccat    900
tggcgctgtc atccactacc tgctgcaggt ggggccagag aagcagaaag agcccttgt    960
gtttgcctcg gtgcggatcc tgggtgcctg gctggcggag agacctcat ccctgcgtaa   1020
ggaggtgtgc caactgctgc ccttccttgt ccgatatgcc aagacactct atgaggaggc   1080
tgaggaggcc agtgacattt cgcagcaggt ggccaacttg ccatctctc ctactacacc   1140
agggccttca tggccagggg atgctctccg gctcctcctt cccggctggt gtcacctgac   1200
tgttgaagat ggtccccggg agattctgat caaggaagga gcccctcac ttctgtgcaa   1260
gtacttcctg cagcagtggg aactcacatc cccgggccat gatacctcgg tgctgccaga   1320
cagcgtggag atcggccttc agacctgttg ccacatcttc ctcaacctgg tggtcaccgc   1380
tccagggctg atcaaacgcg atgcctgctt cacatctctt atgaacaccc tgatgacgtc   1440
actgccctca ctagtgcagc aacaagggag actgcttcta gctgccaacg tggccacttt   1500
ggggctccta atgcccggc tccttagcac ctctccagct ctccaaggaa ccccagcctc   1560
ccgaggtttc ttcgcagctg ccatcctctt tctgtcacag tcccatgtgg cacgagccac   1620
ccctggctct gaccaggcag tgttggccct gtcccctgac tatgaaggca tctgggctga   1680
cttgcaagag ctctggttcc tgggcatgca ggccttcacg ggttgtgtgc cgctgctgcc   1740
ctggctggcc cctgccgccc tgcgctcccg ctggccacag gagctgctac aactgctagg   1800
tagtgtaagc cccaactccg tcaagcctga gatggtggct gcctaccagg gcgtgctggt   1860
ggaattggca cgggctaacc ggctatgccg ggaggccatg aggctgcagg cgggtgaaga   1920
aacggccagc cattaccgaa tggctgcttt ggagcagtgc ctgtcagagc cctgaggggc   1980
atccagtggg tacagaccca ggcgggcagc gagggaagga gggaggaggc atcttccctg   2040
aagcccccaa actggacccc ttcttcagac ccccacaaac accccagctt tctggctttt   2100
ctgagggcta gggcatggtg cccacctctc aagtataaga aactgcatcc tgcctccagc   2160
ccccttgggg cagggattgg cttggaacag aggttggccc cgccaggccg gggaaggttg   2220
gagaagcccc caggaggagg gcaactaagt gtcattatac ccagtgtctg gctccctgat   2280
aggagggagg tcccagggta ggagcgggct ggcaggcgct gactgcctca gcccatgtgc   2340
cctgccggcc agggcgtggc ctccccaagg ctgtggtgcc ccttctggct ccctaggtc   2400
aggtccgcgc cctttaaatt ggccgcttgg cttttgcctt tggtcctctt ggacagagag   2460
caggctcagg ccattgacat cacagttctt ccttttaact ctagtgaccc ggggtccgag   2520
ttgcccctat gcttccaggg caatttggag cagacagacc agtgggggt ggggaacctc   2580
cttccacctg cgcttccttg aggggaccag agagcccttg gtcccaggtc tcttgagctt   2640
ttgtgtcatg ttgcagcaga gtgaagatgg ggggttgggg gttatttatt ttgcttgtcc   2700
ttatccctgc ttggacacct gagcatcaga tccctgtgcc cctggtgcca tctggcctgc   2760
tggagccagg aacaagaggt caccccaccc tagaatccgc atggtttccc tgtgattgca   2820
ctccactgcc accgtggtgc ctggcttcag ctcccctccc ccaatccctg ctaagcctct   2880
actctgcagg gagacgcgac tggcggctcc agcaggaact acctttctga acccgcggag   2940
acccgcataa gcctgacccc ttgcttcctc cccgcccccc agtgcgttct gtgatcgcca   3000
agttcaaagc tgtgcacatg tggacactca ataaatgttt attggtgaaa aaaaaaaaaa   3060
``` aaaaa 3065

<210> SEQ ID NO 4
<211> LENGTH: 579
<212> TYPE: PRT
<213> ORGANISM: Mus sp.

<400> SEQUENCE: 4

```
Met Ile Asp Asp Thr Tyr Gln Cys Leu Thr Ala Val Ala Gly Thr Pro
  1               5                  10                  15

Arg Gly Pro Arg His Leu Ile Ala Gly Thr Val Ser Ala Leu Cys
             20                  25                  30

Gln Ala Tyr Leu Gly His Gly Tyr Gly Phe Asp Gln Ala Leu Ala Leu
             35                  40                  45

Leu Val Gly Leu Leu Ala Ala Ala Glu Thr Gln Cys Trp Lys Glu Ala
         50                  55                  60

Glu Pro Asp Leu Leu Ala Val Leu Arg Gly Leu Ser Glu Asp Phe Gln
 65                  70                  75                  80

Arg Ala Glu Asp Ala Ser Lys Phe Glu Leu Cys Gln Leu Leu Pro Leu
                 85                  90                  95

Phe Leu Pro Pro Thr Thr Val Pro Pro Glu Cys His Arg Asp Leu Gln
                100                 105                 110

Ala Gly Leu Ala Arg Ile Leu Gly Ser Lys Leu Ser Ser Trp Gln Arg
            115                 120                 125

Asn Pro Ala Leu Lys Leu Ala Ala Arg Leu Ala His Ala Cys Gly Ser
        130                 135                 140

Asp Trp Ile Pro Val Gly Ser Ser Gly Ser Lys Phe Leu Ala Leu Leu
145                 150                 155                 160

Val Asn Leu Ala Cys Val Glu Val Arg Leu Ala Leu Glu Glu Thr Gly
                165                 170                 175

Thr Glu Val Lys Glu Asp Val Val Thr Ala Cys Tyr Ala Leu Met Glu
            180                 185                 190

Leu Gly Ile Gln Glu Cys Thr Arg Cys Glu Gln Ser Leu Leu Lys Glu
        195                 200                 205

Pro Gln Lys Val Gln Leu Val Ser Ile Met Lys Glu Ala Ile Gly Ala
    210                 215                 220

Val Ile His Tyr Leu Leu Gln Val Gly Pro Glu Lys Gln Lys Glu Pro
225                 230                 235                 240

Phe Val Phe Ala Ser Val Arg Ile Leu Gly Ala Trp Leu Ala Glu Glu
                245                 250                 255

Thr Ser Ser Leu Arg Lys Glu Val Cys Gln Leu Leu Pro Phe Leu Val
            260                 265                 270

Arg Tyr Ala Lys Thr Leu Tyr Glu Glu Ala Glu Ala Ser Asp Ile
        275                 280                 285

Ser Gln Gln Val Ala Asn Leu Ala Ile Ser Pro Thr Thr Pro Gly Pro
    290                 295                 300

Ser Trp Pro Gly Asp Ala Leu Arg Leu Leu Pro Gly Trp Cys His
305                 310                 315                 320

Leu Thr Val Glu Asp Gly Pro Arg Glu Ile Leu Ile Lys Glu Gly Ala
                325                 330                 335

Pro Ser Leu Leu Cys Lys Tyr Phe Leu Gln Gln Trp Glu Leu Thr Ser
            340                 345                 350

Pro Gly His Asp Thr Ser Val Leu Pro Asp Ser Val Glu Ile Gly Leu
        355                 360                 365
```

```
Gln Thr Cys Cys His Ile Phe Leu Asn Leu Val Val Thr Ala Pro Gly
    370                 375                 380
Leu Ile Lys Arg Asp Ala Cys Phe Thr Ser Leu Met Asn Thr Leu Met
385                 390                 395                 400
Thr Ser Leu Pro Ser Leu Val Gln Gln Gln Gly Arg Leu Leu Leu Ala
                405                 410                 415
Ala Asn Val Ala Thr Leu Gly Leu Leu Met Ala Arg Leu Leu Ser Thr
            420                 425                 430
Ser Pro Ala Leu Gln Gly Thr Pro Ala Ser Arg Gly Phe Phe Ala Ala
            435                 440                 445
Ala Ile Leu Phe Leu Ser Gln Ser His Val Ala Arg Ala Thr Pro Gly
            450                 455                 460
Ser Asp Gln Ala Val Leu Ala Leu Ser Pro Asp Tyr Glu Gly Ile Trp
465                 470                 475                 480
Ala Asp Leu Gln Glu Leu Trp Phe Leu Gly Met Gln Ala Phe Thr Gly
                485                 490                 495
Cys Val Pro Leu Leu Pro Trp Leu Ala Pro Ala Ala Leu Arg Ser Arg
                500                 505                 510
Trp Pro Gln Glu Leu Leu Gln Leu Leu Gly Ser Val Ser Pro Asn Ser
            515                 520                 525
Val Lys Pro Glu Met Val Ala Ala Tyr Gln Gly Val Leu Val Glu Leu
            530                 535                 540
Ala Arg Ala Asn Arg Leu Cys Arg Glu Ala Met Arg Leu Gln Ala Gly
545                 550                 555                 560
Glu Glu Thr Ala Ser His Tyr Arg Met Ala Ala Leu Glu Gln Cys Leu
                565                 570                 575
Ser Glu Pro

<210> SEQ ID NO 5
<211> LENGTH: 1808
<212> TYPE: DNA
<213> ORGANISM: Homo sapiens

<400> SEQUENCE: 5
atgatcgatg acacctacca gtgcctgaca gctgttgcgg gcacacccg agggccccgg      60 cacctcattg ctggtggcac cgtgtctgcc ctgtgccagg cgtacctggg gcatggctac     120
ggctttgacc aggctctggc actcttggtg gggctgctgg ctgctgcaga gacacagtgc     180
tggaaggagg cggagcccga cctgctggct gtgttgcgag gcctcagtga ggatttccaa     240
agagccgaag atgccagcaa gtttgagctc tgccagctgc tgcccctttt tctgccccca     300
acaactgtgc cccctgaatg ccaccgagat ctgcaggctg gctggcacg aatcctagga      360 agcaagttga gctcctggca gcgcaaccct gcactgaagc tggcagcccg cctggctcat     420
gcctgcggct ccgactggat cccagtgggc agctctggga gcaagtttct ggccctgctc     480
gtgaatctgg cgtgcgtgga ggtacggctg ctctcgagg agacaagcac agaggtgaaa      540
gaagacgtgg taacagcctg ctatgccctt atggaattgg ggatccagga gtgcaccgc      600 tgtgagcagt ccctgcttaa ggagccacag aaggttcagc tcgtgagcat tatgaaagag     660
gccattggcg ctgtcatcca ctacctgctg caggtggggc cagagaagca gaaagagccc     720
tttgtgtttg cctcggtgcg gatcctgggt gcctggctgg cggaggagac ctcatccctg     780
cgtaaggagg tgtgccaact gctgcccttc cttgtccgat atgccaagac actctatggg     840
gaggctgagg aggccagtga catttcgcag caggtggcca acttggccat ctctcctact     900
```

-continued

```
acaccagggc cttcatggcc agggggatgct ctccggctcc tccttcccgg ctggtgtcac      960
ctgactgttg aagatggtcc ccgggagatt ctgatcaagg aaggagcccc ctcacttctg     1020
tgcaagtact tcctgcagca gtgggaactc acatccccgg ccatgatac ctcggtgctg      1080 ccagacagcg tggagatcgg ccttcagacc tgttgccaca tcttcctcaa cctggtggtc     1140
accgctccag ggctgatcaa acgcgatgcc tgcttcacat ctcttatgaa cacctgatg    1200 acgtcactgc cctcactagt gcagcaacaa gggagactgc ttctagctgc caacgtggcc   1260
actttggggc tcctaatggc ccggctcctt agcacctctc cagctctcca aggaaccca   1320 gcctcccgag gtttcttcgc agctgccatc ctctttctgt cacagtccca tgtggcacga    1380
gccacccctg gctctgacca ggcagtgttg gccctgtccc ctgactatga aggcatctgg    1440
gctgacttgc aagagctctg gttcctgggc atgcaggcct tcacggttg tgtgccgctg    1500 ctgccctggc tggcccctgc cgccctgcgc tcccgctggc cacaggagct gctacaactg    1560
ctaggtagtg taagccccaa ctccgtcaag cctgagatgg tggctgccta ccagggcgtg    1620
ctggtggaat tggcacgggc taaccggcta tgccggagg ccatgaggct gcaggcgggt    1680
gaagaaacgg ccagccatta ccgaatggct gctttggagc agtgcctgtc agagccctga   1740
ggggcatcca gtgggtacag acccaggcgg gcagcgaggg aaggagggag gaggcatctt   1800
ccctgaag                                                            1808
```

<210> SEQ ID NO 6
<211> LENGTH: 579
<212> TYPE: PRT
<213> ORGANISM: Homo sapiens

<400> SEQUENCE: 6

```
Met Ile Asp Asp Thr Tyr Gln Cys Leu Thr Ala Val Ala Gly Thr Pro
  1               5                  10                  15

Arg Gly Pro Arg His Leu Ile Ala Gly Gly Thr Val Ser Ala Leu Cys
                 20                  25                  30

Gln Ala Tyr Leu Gly His Gly Tyr Gly Phe Asp Gln Ala Leu Ala Leu
             35                  40                  45

Leu Val Gly Leu Leu Ala Ala Ala Glu Thr Gln Cys Trp Lys Glu Ala
         50                  55                  60

Glu Pro Asp Leu Leu Ala Val Leu Arg Gly Leu Ser Glu Asp Phe Gln
 65                  70                  75                  80

Arg Ala Glu Asp Ala Ser Lys Phe Glu Leu Cys Gln Leu Leu Pro Leu
                 85                  90                  95

Phe Leu Pro Pro Thr Thr Val Pro Pro Glu Cys His Arg Asp Leu Gln
                100                 105                 110

Ala Gly Leu Ala Arg Ile Leu Gly Ser Lys Leu Ser Ser Trp Gln Arg
            115                 120                 125

Asn Pro Ala Leu Lys Leu Ala Ala Arg Leu Ala His Ala Cys Gly Ser
        130                 135                 140

Asp Trp Ile Pro Val Gly Ser Gly Ser Lys Phe Leu Ala Leu Leu
145                 150                 155                 160

Val Asn Leu Ala Cys Val Glu Val Arg Leu Ala Leu Glu Glu Thr Ser
                165                 170                 175

Thr Glu Val Lys Glu Asp Val Val Thr Ala Cys Tyr Ala Leu Met Glu
            180                 185                 190

Leu Gly Ile Gln Glu Cys Thr Arg Cys Glu Gln Ser Leu Leu Lys Glu
        195                 200                 205
```

```
Pro Gln Lys Val Gln Leu Val Ser Ile Met Lys Glu Ala Ile Gly Ala
    210                 215                 220
Val Ile His Tyr Leu Leu Gln Val Gly Pro Glu Lys Gln Lys Glu Pro
225                 230                 235                 240
Phe Val Phe Ala Ser Val Arg Ile Leu Gly Ala Trp Leu Ala Glu Glu
                245                 250                 255
Thr Ser Ser Leu Arg Lys Glu Val Cys Gln Leu Leu Pro Phe Leu Val
            260                 265                 270
Arg Tyr Ala Lys Thr Leu Tyr Gly Glu Ala Glu Ala Ser Asp Ile
        275                 280                 285
Ser Gln Gln Val Ala Asn Leu Ala Ile Ser Pro Thr Thr Pro Gly Pro
    290                 295                 300
Ser Trp Pro Gly Asp Ala Leu Arg Leu Leu Leu Pro Gly Trp Cys His
305                 310                 315                 320
Leu Thr Val Glu Asp Gly Pro Arg Glu Ile Leu Ile Lys Glu Gly Ala
                325                 330                 335
Pro Ser Leu Leu Cys Lys Tyr Phe Leu Gln Gln Trp Glu Leu Thr Ser
            340                 345                 350
Pro Gly His Asp Thr Ser Val Leu Pro Asp Ser Val Glu Ile Gly Leu
        355                 360                 365
Gln Thr Cys Cys His Ile Phe Leu Asn Leu Val Val Thr Ala Pro Gly
    370                 375                 380
Leu Ile Lys Arg Asp Ala Cys Phe Thr Ser Leu Met Asn Thr Leu Met
385                 390                 395                 400
Thr Ser Leu Pro Ser Leu Val Gln Gln Gly Arg Leu Leu Leu Ala
                405                 410                 415
Ala Asn Val Ala Thr Leu Gly Leu Leu Met Ala Arg Leu Leu Ser Thr
            420                 425                 430
Ser Pro Ala Leu Gln Gly Thr Pro Ala Ser Arg Gly Phe Phe Ala Ala
        435                 440                 445
Ala Ile Leu Phe Leu Ser Gln Ser His Val Ala Arg Ala Thr Pro Gly
    450                 455                 460
Ser Asp Gln Ala Val Leu Ala Leu Ser Pro Asp Tyr Glu Gly Ile Trp
465                 470                 475                 480
Ala Asp Leu Gln Glu Leu Trp Phe Leu Gly Met Gln Ala Phe Thr Gly
                485                 490                 495
Cys Val Pro Leu Leu Pro Trp Leu Ala Pro Ala Ala Leu Arg Ser Arg
            500                 505                 510
Trp Pro Gln Glu Leu Leu Gln Leu Leu Gly Ser Val Ser Pro Asn Ser
        515                 520                 525
Val Lys Pro Glu Met Val Ala Ala Tyr Gln Gly Val Leu Val Glu Leu
    530                 535                 540
Ala Arg Ala Asn Arg Leu Cys Arg Glu Ala Met Arg Leu Gln Ala Gly
545                 550                 555                 560
Glu Glu Thr Ala Ser His Tyr Arg Met Ala Ala Leu Gly Gln Cys Leu
                565                 570                 575
Ser Glu Pro
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer -continued

<400> SEQUENCE: 7
atccttagca cattccttac                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 8
agaaacttgc tcccagagct                                            20

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 9
tgaaggtcgg tgtgaacgga tttggc                                     26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 10
catgtaggcc atgaggtcca ccac                                       24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 11
atgatcgatg acacctacca gtgc                                       24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 12
cttcagggaa gatgcctcct                                            20

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 13
agccagggtg cccccggtct tcagggaa                                   28

<210> SEQ ID NO 14
<211> LENGTH: 24

-continued

```
<212> TYPE: DNA
<213> ORGANISM: Artificial Sequence
<220> FEATURE:
<223> OTHER INFORMATION: Description of Artificial Sequence:primer

<400> SEQUENCE: 14
cttggccccg ggagcaccat ccct                                              24
```

PROTEIN C16 AND C16N OR GENES ENCODING THE SAME

This application is the national phase under 35 U.S.C. §371 of prior PCT International Application No. PCT/JP97/01391 which has an International filing date of Apr. 23, 1997 which designated the United States of America, the entire contents of which are hereby incorporated by reference.

TECHNICAL FIELD

The present invention relates to novel proteins C16 and C16N or variant proteins thereof as well as genes encoding the same. More particularly, the present invention relates to novel proteins C16 and C16N which have activities of inducing cells to become capable of resorbing hydroxyapatite (this activity is hereinafter sometimes briefly referred to as "hydroxyapatite-resorbing activity"), supporting survival of neuron, inhibiting proliferation of osteoblast, and/or promoting expression of type I collagen in osteoblast and which can therefore be used as pharmaceutical agents or in screening for developing new drugs, or to variant proteins thereof, and to genes encoding the same.

BACKGROUND ART

Metabolic regulation of calcium in blood is absolutely essential for survival, and the concentration is maintained constant quite strictly. When the blood calcium concentration is increased by some reason, it causes various diseases such as hypertension, arteriosclerosis, diabetes, myocardial infarction, and hypercalcemia. On the other hand, decrease in blood calcium concentration also results in diseases such as hypocalcemia. In addition, substantial decrease in blood calcium concentration due to, for example, massive hemorrhage or radiation exposure may sometimes lead to death.

As cells responsible for quite important regulation of blood calcium concentration, which is quite important in vivo, osteoclast is presently known. Osteoclast is considered to directly regulate the calcium concentration in blood by resorbing bone (bone matrix) and releasing calcium into blood. In mammals, however, there are only about 50,000 osteoclasts in vivo. On the contrary, there are about 25,000 osteocytes, even in 1 mm$^3$ of bone, embedded in calcified hard tissues reserving calcium. Population of osteoclasts is therefore considered too small to regulate the calcium concentration in blood (Kumegawa et al., *Molecular Medicine*, 30, p.1254 (1993) and Ozawa et al., *Nihon-Rinsho*, vol. 52, No. 9, p. 2246 (1994)).

Furthermore, because there are no osteoclasts in op/op mouse which is a model animal for osteopetrosis, the primary function of osteoclast, bone remodeling, scarcely occurs in this animal. Despite the absence of osteoclast, however, the blood calcium concentration is maintained normally in this animal (*Molecular Medicine*, Vol. 30, No. 10, p. 1240 (1993)).

This fact suggests that the regulation of the blood calcium concentration by osteoclast is just supplemental and there may exist some other cells which dominantly regulate the calcium concentration in blood. Although such cells have not yet been identified, if any factors which grow such cells or which induce cells to produce such cells are found, the factors themselves or inhibitors thereof are expected to be useful as therapeutic agents for various diseases caused by abnormality in blood calcium concentration as described above. Although identification of such factor has been desired, its successful cloning has not yet been reported.

DISCLOSURE OF THE INVENTION

The present inventors have long investigated for factors inducing cells into osteoclast, by expression cloning from BW5147 which is a cancer cell having bone metastasis ability (hereinafter simply referred to as "bone metastatic cell"). Specifically, the investigation is carried out as follows: mRNA isolated from BW5147 cell is injected into Xenopus oocyte to be translated, and the translated product (protein) is applied to mouse bone marrow cells in order to determine whether or not the differentiation of the bone marrow cell into osteoclast is induced. In particular, for the purpose of our study, cells which have the four known properties of osteoclast, i.e. (1) TRAP stainability, (2) the presence of calcitonin receptor, (3) resorbing activity on dentine slice, and (4) hydroxyapatite-resorbing activity are identified as "osteoclast", and factors which induce cells to become said osteoclast are identified as "differentiation-inducing factors for osteoclast" in our study.

In the process of this expression cloning, we found a novel proteinaceous factor of great interest. Specifically, the factor exhibits only the activity (4) among the above-noted activities (1)–(4), and does not have the other activities (1)–(3). This is a factor different from differentiation-inducing factors for osteoclast because it exhibits only the activity (4). In addition, since it has the activity (4), i.e. the activity of inducing cells to become capable of resorbing hydroxyapatite (crystalline calcium in bone), the factor is expected to be a novel factor capable of inducing cells regulating the blood calcium concentration, which has not yet been identified (such factor is hereinafter sometimes simply referred to as "regulating factor for blood calcium concentration").

We designated this novel proteinaceous factor as "C16". Surprisingly, further investigations on this factor C16 revealed that the gene corresponding to the factor C16 is exclusively expressed in bone and brain, and that the factor C16 also has activities of supporting survival of neuron, inhibiting proliferation of osteoblast, and promoting expression of type I collagen in osteoblast.

An example of such multifunctional proteinaceous factors having two or more activities is FGF (Fibroblast Growth Factor). Since relatively large amount of FGF is present in embryo, postnatal brain (Risau et al. *EMBO J.*, 7, p. 959 (1988); Gospadarowicz et al., *Methods Enzymol.*, 147, p. 106 (1987)) and hypophysis, it has been considered that FGF plays some role also in central nervous system in addition to its function as a fibroblast growth factor. In recent years, many studies have been reported, showing that FGF has a neurotrophic activity. In studies using primary neuron culture, it has been shown that FGF has an activity of supporting survival of neuron in hippocampus, cerebral cortex, corpus striatum, septulum, thalamus, midbrain, and spinal cord (Naruo et al., *J. Biol. Chem.*, 268, p. 2857 (1993)). In the light of such versatility of FGF, it is expected that the factor C16 which we found may also be a versatile factor having multiple functions, such as function inducing cells to become capable of resorbing hydroxyapatite, function supporting survival of neuron, function inhibiting proliferation of osteoblast, and function promoting expression of type I collagen in osteoblast.

Furthermore, we also screened cDNA libraries for factors analogous to C16 using C16 DNA as a probe or primer, and found a new proteinaceous factor which comprises the region from position 1 to 245 of the amino acid sequence of C16 (SEQ ID NO: 2) and additional 334 amino acids linked to its C-terminus. We designated this factor as "C16N". Like the factor C16, C16N also has the hydroxyapatite-resorbing activity, and activities of supporting survival of neuron, inhibiting proliferation of osteoblast, and promoting expression of type I collagen in osteoblast. Thus, it was shown that C16N also falls within the scope of the present invention as a factor of the same kind as C16.

The present invention has been accomplished on the basis of the findings as described above.

Thus, the gist of the present invention is:

(1) C16 DNA comprising the base sequence shown in SEQ ID NO: 1;

(2) C16 protein comprising the amino acid sequence shown in SEQ ID NO: 2;

(3) DNA encoding a protein which contains insertion, deletion, or substitution of one or more amino acids in the protein of the above item (2), and which protein has the following properties (i), (ii), (iii), and/or (iv):
  (i) having activity of inducing cells to become capable of resorbing hydroxyapatite;
  (ii) having activity of supporting survival of neuron;
  (iii) having activity of inhibiting proliferation of osteoblast;
  (iv) having activity of promoting expression of type I collagen in osteoblast.

(4) DNA which hybridizes under stringent conditions to DNA of the above item (1) and which encodes a protein having the following properties (i), (ii), (iii), and/or (iv):
  (i) having activity of inducing cells to become capable of resorbing hydroxyapatite;
  (ii) having activity of supporting survival of neuron;
  (iii) having activity of inhibiting proliferation of osteoblast;
  (iv) having activity of promoting expression of type I collagen in osteoblast.

(5) DNA encoding a protein which contains at least the region from position 1 to 245 of the amino acid sequence of the above item (2), and which protein has the following properties (i), (ii), (iii), and/or (iv):
  (i) having activity of inducing cells to become capable of resorbing hydroxyapatite;
  (ii) having activity of supporting survival of neuron;
  (iii) having activity of inhibiting proliferation of osteoblast;
  (iv) having activity of promoting expression of type I collagen in osteoblast.

(6) C16N DNA comprising the base sequence shown in SEQ ID NO: 3 or 5;

(7) protein encoded by DNA of any one of the above items (3)–(6);

(8) C16N protein comprising the amino acid sequence shown in SEQ ID NO: 4 or 6;

(9) expression vector containing DNA of any one of the above items (1) and (3)–(6);

(10) transformant transformed with the expression vector of the above item (9);

(11) process for producing a recombinant protein, said process being characterized in that it comprises culturing the transformant of the above item (10) under conditions in which the expression vector of the above item (9) can be expressed;

(12) pharmaceutical agent which contains as an active ingredient the protein of the above item (2), (7), or (8);

(13) partial peptide of the protein of the above item (2), (7), or (8) comprising at least 6 amino acids or more

(14) antibody against the protein of the above item (2), (7), or (8), or against the partial peptide of the above item (13);

(15) method for screening inhibitors of C16 or C16N activity, which method is characterized in that the protein of the above item (2), (7), or (8) is used;

(16) inhibitor of C16 or C16N activity obtained by the screening method of the above item (15);

(17) inhibitor of C16 or C16N activity of the above item (16) which comprises the partial peptide of the above item (13) or the antibody of the above item (14); and

(18) transgenic animal in which DNA of any one of the above items (1) and (3)–(6) has been artificially inserted into its chromosome, or has been deleted from the chromosome.

THE MODES FOR CARRYING OUT THE INVENTION

The first embodiment of the present invention provides DNA comprising the base sequence shown in SEQ ID NO: 1, that is, cDNA encoding a typical protein of the present invention, C16.

The cDNA may be obtained by, for example, "expression cloning" as described below.

Since bone metastatic cells may be expected to produce factor(s) which induce cells to become capable of regulating the blood calcium concentration in addition to differentiation-inducing factors for osteoclast, total RNA is firstly prepared from such bone metastatic cells and mRNA is then prepared from the total RNA. An example of bone metastatic cells used herein is mouse BW5147 cell line. Total RNA may be obtained using one of conventional methods such as AGPC method (acid guanidium thiocyanate-phenol-chloroform method; Tuji and Nakamura, *JIKKEN-IGAKU*, 9, p. 99 (1991)). mRNA may be prepared by, for example, the method described in *Molecular Cloning*, 2nd ed., Cold Spring Harbor Laboratory Press (1989), using oligo-dT cellulose column.

Next, cDNA library is prepared from mRNA thus obtained. cDNA library may be prepared from total mRNA, or from mRNA fraction comprising part of the total mRNA. The mRNA fraction may be prepared by fractionating total mRNA using one of conventional methods such as sucrose density gradient centrifugation, and collecting the fractions exhibiting hydroxyapatite-resorbing activity, and preceding and succeeding fractions (see below regarding assay for hydroxyapatite-resorbing activity). cDNA library may be prepared by one of conventional methods, for example, as described by Gubler and Hoffman (*Gene*, 25, p. 263 (1983)).

The above cDNA library is then divided into multiple pools. The number of cDNA clones per pool may be determined arbitrarily depending on the number of independent clones constituting the cDNA library. For example, in the case of cDNA library containing about $6 \times 10^5$ independent clones, it may be preferred for subsequent procedures to divide it into about 60 pools each of which contains $1 \times 10^4$ clones.

The DNAs are then prepared from each pool in the usual manner, and cRNAs are prepared using these DNAs as templates. cRNAs can be easily prepared, for example, by using commercially available mRNA capping kit (Stratagene).

The cRNAs are then translated into proteins by injecting the cRNAs from each pool into Xenopus oocyte. For example, the injection into oocyte may be carried out as follows. Oocyte mass is removed from female Xenopus having body length of about 10 cm. The oocyte cells are then separated from each other under microscope, and intact living cells at stage V or VI are selected. Into these oocyte cells, cRNAs are injected through capillary using digital micro-dispenser or the like. The amount of the cRNA to be injected per oocyte is preferably 50 nl or less. After culture of the oocytes for several days, the culture supernatant is harvested. The translated products (proteins) from cRNAs are found in the supernatant, and therefore, it can be used as a sample for assay.

Using the culture supernatant sample, the following assay is then conducted.

It is preferred to use bone marrow cells for this assay, since the cells regulating the blood calcium concentration is presumed to be differentiated and induced from bone marrow cells, like osteoclast. In particular, epiphyses of femur and shank of 6–12 week old mouse are cut off, and bone marrow cells are extruded once from each end with 1 ml of α-MEM medium using a syringe equipped with 26G needle. After pipetting and removing the precipitated bone debris, the supernatant can be used as bone marrow cells. The bone marrow cells thus prepared are suspended in a culture medium containing activated vitamin D to obtain an appropriate concentration (e.g., $2 \times 10^6$ cells/ml), and charged onto a plate (such as 96-well plate). To the plate, the samples of Xenopus culture supernatant described above are added to conduct the assays as follows: using the four known methods for the identification of osteoclast, i.e., 1) TRAP staining, 2) pit formation assay using dentine slice, 3) pit formation assay using Osteologic (hydroxyapatite) well, and 4) detection of calcitonin receptor, pools which are active only in 3) are selected.

The pools judged positive in these assays are further divided into subpools, and similar procedures can be repeated until clones encoding C16, a typical protein of the present invention, are obtained. The above assays 1)–4) are all known, and see Examples 2.3.1–2.3.4 for details.

The base sequence of C16 cDNA cloned by expression cloning as described above may be determined by means of a sequencer using, for example, Auto Read Sequencing kit (Pharmacia), or by means of RI using BcaBEST Sequencing kit (TaKaRa) based on the dideoxy method.

Alternatively, by the use of the base sequence of C16 cDNA herein disclosed, the C16 cDNA can be easily prepared using the cDNA in whole or in part as a probe or PCR primer, instead of the above "expression cloning". Furthermore, C16 cDNA may also be obtained by conducting site-directed mutagenesis (M. J. Zoller et al., *Methods in Enzymology*, 100, p. 468 (1983)) or PCR (*Molecular Cloning*, 2nd ed., Chapter 15, Cold Spring Harbor Laboratory Press (1989)) on C16N cDNA of the present invention described below.

The second embodiment of the present invention is C16 which is a typical protein of the present invention having the amino acid sequence shown in SEQ ID NO: 2. The factor C16 is a protein encoded by the longest open reading frame (positions 236–1234 of SEQ ID NO: 1) of C16 cDNA shown in SEQ ID NO: 1. It has been confirmed that the molecular weight of C16 calculated from this longest open reading frame is consistent with that of the product of C16 gene obtained by its in vitro translation (about 40 kDa).

The factor C16 can be expressed and produced by ligating the cloned C16 cDNA into one of known expression vectors such as pBK-CMV, and then introducing it into appropriate host cells. Host cells may be prokaryotic or eukaryotic, and for example *E. coli* strains and animal cell lines are already used widely for such purpose, and they are readily available unless otherwise stated. Examples of animal host cells may include COS-1, COS-7, and CHO cells. Suitable animal host cells may be transformed with expression plasmids using known methods such as LIPOFECTIN method (Felgner P. L. et al., *Proc. Natl. Acad. Sci. USA*, 84, p. 7413 (1987)). Since culture supernatant of transformed cells contains a sufficient amount of C16 to be used as such in various assays after appropriate dilution, it can be used for measurements of activities, such as hydroxyapatite-resorbing activity, activity of supporting survival of neuron, activity of inhibiting proliferation of osteoblast, and/or activity of promoting expression of type I collagen in osteoblast. As for methods for measuring the activities, see the third embodiment of the present invention described below.

C16 produced in culture supernatant can be easily purified by known procedures using zinc chelate agarose, concanavalin A agarose, Sephadex G-150 and the like.

The third embodiment of the present invention is DNA encoding so-called modified protein which contains insertion, deletion, or substitution of one or more amino acids in C16 shown in SEQ ID NO: 2, and which protein has (i) activity of inducing cells to become capable of resorbing hydroxyapatite, (ii) activity of supporting survival of neuron, (iii) activity of inhibiting proliferation of osteoblast, and/or (iv) activity of promoting expression of type I collagen in osteoblast.

In this connection, one skilled in the art can easily introduce insertion, deletion, or substitution of one or more amino acids using genetic engineering techniques, for example, by site-directed mutagenesis (M. J. Zoller et al., *Methods in Enzymology*, 100, p. 468 (1983)) or PCR method (*Molecular Cloning*, 2nd ed., Chapter 15, Cold Spring Harbor Laboratory Press (1989)). The phrase "insertion, deletion, or substitution of one or more amino acids" herein means that the number of amino acids that can be inserted, deleted, or substituted by well-known methods such as site-directed mutagenesis described above are inserted, deleted, or substituted.

Activity of inducing cells to become capable of resorbing hydroxyapatite (i.e., hydroxyapatite-resorbing activity) may be easily measured, for example, in the following manner. Bone marrow cells are cultured in wells coated with hydroxyapatite (trade name: osteologic; manufactured by MILLENIUM BIOLOGIX) (see the second embodiment of the present invention regarding the method for culturing bone marrow cells), and protein to be assayed (i.e., expressed protein obtained by ligating DNA of the third embodiment of the present invention to a well-known expression vector and introducing the vector into an appropriate host) is added thereto. At intervals of 3–4 days, about three quarters of the medium are replaced with a flesh medium, and the protein is newly added. After one week, the cells are removed by treating the wells with 20% sodium hypochlorite, and the number of pits on each well can be converted into mesh number per pit to evaluate the hydroxyapatite-resorbing activity (bone-resorbing activity) of the differentiated cells induced from bone marrow cells. By subjecting various modified proteins produced above to such assay, modified proteins of the invention which have hydroxyapatite-resorbing activity can be easily selected.

Activity of supporting survival of neuron can be easily measured, for example, in the following manner. For example, PC12D cells are cultured in RPMI 1640 medium containing 5% fetal bovine serum and 5% heat-inactivated horse serum. To assay the activity, the cells are plated onto 24- or 96-well plate at $1-3 \times 10^5$ cells/ml in serum-free medium, and various proteins encoded by DNA of the third embodiment of the present invention are added thereto. The number of living cells after 72 hours is compared to that observed in culture without proteins, and if more than two-fold cells survive, the protein is judged to have the activity. As positive control, NGF may be added at the final concentration of 24 ng/ml. Similarly, granule cells of cerebellum or neurons of hippocampus can be used instead of PC12D cells.

In addition to the activity of supporting survival of neuron, it is also important from a different standpoint to measure an activity of promoting adhesion between neurons. Thus, during the development of brain, neurons migrate from the place where it was born, and they elongate axons during the migration or after reached their final goal, to form complex neural network. Specificity of synaptic connection is determined through strict control of such migration and axon elongation, and it has been shown that some molecules on the cell surface are responsible for the recognition of the associated neurons in this process (Watanabe et al., SEIKAGAKU, 68, (9), p. 1548 (1996)). Factors which can promote such recognition between neurons, i.e. "adhesion", are very likely to play an important role in morphogenesis and higher functions of brain. Thus, measurement of an activity of promoting adhesion between neurons may also be important in the light of maintenance of neurons in vivo. This activity can be measured using the same assay system as described above (see Example 13-2).

Activity of inhibiting proliferation of osteoblast can be measured according to the procedures described in Example 14, and activity of promoting expression of type I collagen in osteoblast can be measured according to the procedures described in Example 15.

By subjecting various modified proteins prepared above to the assays as describe above, the modified proteins of the present invention which have activities of supporting survival of neuron, inhibiting proliferation of osteoblast, or promoting expression of type I collagen in osteoblast can be easily selected.

The above activities, that is, "activity of inducing cells to become capable of resorbing hydroxyapatite", "activity of supporting survival of neuron", "activity of inhibiting proliferation of osteoclast", and "activity of promoting expression of type I collagen in osteoblast", are the properties of C16, a typical protein of the present invention shown n SEQ ID NO: 2. Accordingly, all of the modified proteins which contain insertion, deletion, or substitution of one or more amino acids in C16 and which have "activity of inducing cells to become capable of resorbing hydroxyapatite", "activity of supporting survival of neuron", "activity of inhibiting proliferation of osteoclast", and/or "activity of promoting expression of type I collagen in osteoblast", retain the essence of the present invention, and therefore, they are included in the present invention. Specific examples of such DNA of the third embodiment of the present invention include mouse C16N DNA comprising the base sequence shown in SEQ ID NO: 3, human C16N DNA comprising the base sequence shown in SEQ ID NO: 5, altered mouse C16N DNA in which A (alanine) is substituted for G (guanine) at position 724 in SEQ ID NO: 3, altered human C16N DNA in which A is substituted for G at position 489 in SEQ ID NO: 5, DNAs which encode the modified proteins of C16N, and the like (these C16N DNAs and others are described later).

The fourth embodiment of the present invention is DNA which hybridizes under stringent conditions to DNA comprising the base sequence shown in SEQ ID NO: 1 and which encodes a protein having (i) activity of inducing cells to become capable of resorbing hydroxyapatite, (ii) activity of supporting survival of neuron, (iii) activity of inhibiting proliferation of osteoblast, and/or (iv) activity of promoting expression of type I collagen in osteoblast.

As used herein, "DNA which hybridizes under stringent conditions" refers to DNA which hybridizes to DNA of SEQ ID NO: 1 under standard conditions for hybridization such as those described in Example 10 (formamide concentration: 50%, salt concentration: 5×SSC, temperature: ca. 42° C.).

Such DNA is cloned, for example, by hybridization with DNA shown in SEQ ID NO: 1. Particular procedures for preparation of cDNA library, hybridization, selection of positive colonies, base sequencing and the like are all well known, and easily performed by making reference to, for example, *Molecular Cloning*, 2nd ed., Cold Spring Harbor Laboratory Press (1989). Examples of cDNA library are those derived from human brain or thalamus. An example of the probe used in the hybridization is DNA having the base sequence shown in SEQ ID NO: 1.

The activities described in the above items (i)–(iv), that is, activities of inducing cells to become capable of resorbing hydroxyapatite, supporting survival of neuron, inhibiting proliferation of osteoblast, and promoting expression of type I collagen in osteoblast, respectively, can be easily measured by the assays described above for the third embodiment of the present invention. By subjecting various proteins encoded by DNAs which hybridizes under stringent conditions to C16 DNA to such assay systems, proteins having similar activities to those of C16 can also be easily selected.

The above activities, that is, "activity of inducing cells to become capable of resorbing hydroxyapatite", "activity of supporting survival of neuron", "activity of inhibiting proliferation of osteoclast", and "activity of promoting expression of type I collagen in osteoblast", are the properties of C16, a typical protein of the present invention shown in SEQ ID NO: 2. Accordingly, all of the DNAs which hybridize under stringent conditions to DNA comprising the base sequence shown in SEQ ID NO: 1 and which have any one of the above activities retain the essence of the present invention, and therefore, they are included in the present invention. Specific examples of such DNA of the fourth embodiment of the present invention include mouse C16N DNA comprising the base sequence shown in SEQ ID NO: 3, human C16N DNA comprising the base sequence shown in SEQ ID NO: 5, altered mouse C16N DNA in which A is substituted for G at position 724 in SEQ ID NO: 3, altered human C16N DNA in which A is substituted for G at position 489 in SEQ ID NO: 5, C16N DNAs derived from other species, and the like. Such C16N DNAs and others are described below.

As described in the section "DISCLOSURE OF THE INVENTION", cDNA libraries derived from whole brain, thalamus, and the like were screened for factors analogous to C16 using the full length C16 gene (SEQ ID NO: 1) as a probe, and a related factor which hybridized to this probe under stringent conditions was cloned. Analysis of this factor revealed that it contained the region from position 1 to 245 of the C16 amino acid sequence shown in SEQ ID NO: 2 and further contains 334 amino acids linked to C-terminus. We designated this factor "C16N". As far as DNA construction is concerned, C16N DNA possesses quite similar structure to that of C16 DNA, having the same base sequence as shown in SEQ ID NO: 1, with the exceptions that it contains insertion of one base (G) between G at position 970 and T (thymine) at position 971, and insertion of 153 bases between A at position 1137 and C (cytosine) at position 1138, and that G is substituted for A at position 1155, and C is substituted for T at position 1200, in C16 DNA shown in SEQ ID NO: 1. Those skilled in the art will readily understand that this C16N DNA is included in the fourth embodiment of the present invention, because it hybridizes to C16 DNA under stringent conditions as described above, and it has activities similar to those of C16, that is, hydroxyapatite-resorbing activity, and activities of supporting survival of neuron, inhibiting proliferation of osteoblast, and promoting expression of type I collagen in osteoblast. In addition, since human and mouse C16Ns show extremely high homology (99.7%), C16N derived from other species should also hybridize to C16 DNA under stringent conditions, like human and mouse C16Ns. Thus, such C16N DNAs derived from other species are also included in the fourth embodiment of the present invention. Furthermore, during the cloning of C16N gene, we have also cloned an altered mouse C16N DNA in which A is substituted for G at position 724 in SEQ ID NO: 3, and an altered human C16N DNA in which A is substituted for G at position 489 in SEQ ID NO: 5. These DNAs are also included in the fourth embodiment of the present invention.

The fifth embodiment of the present invention is DNA encoding a protein which contains at least the region from position 1 to 245 of the amino acid sequence shown in SEQ ID NO: 2, and which protein has (i) activity of inducing cells to become capable of resorbing hydroxyapatite, (ii) activity of supporting survival of neuron, (iii) activity of inhibiting proliferation of osteoblast, and/or (iv) activity of promoting expression of type I collagen in osteoblast.

As described above, C16 and the newly cloned factor C16N share the same amino acid sequence from their position 1 to 245, and they both exhibit the above activities (i), (ii), (iii), and (iv). These findings indicate that this very N-terminal region from position 1 to 245 is responsible for the activities. In other words, the findings indicate that proteins will exhibit the activities only if they contain at least the region from position 1 to 245. Accordingly, all the proteins which contain at least the region from position 1 to 245 of the C16 or C16N amino acid sequence, and which have the activities (i), (ii), (iii) and/or (iv), retain the essence of the present invention, and therefore, they are included in the present invention.

DNA of the fifth embodiment of the present invention can be easily prepared, for example, by PCR using appropriate primers. Such PCR may be conducted by making reference to *Molecular Cloning*, 2nd ed., Chapter 15, Cold Spring Harbor Laboratory Press (1989) or the like. The activities (i), (ii), (iii), and (iv) can be easily measured by the assays described above for the third embodiment of the present invention.

Specific examples of such DNA of the fifth embodiment of the present invention include mouse C16N DNA comprising the base sequence shown in SEQ ID NO: 3, human C16N DNA comprising the base sequence shown in SEQ ID NO: 5, altered mouse C16N DNA in which A is substituted for G at position 724 in SEQ ID NO: 3, altered human C16N DNA in which A is substituted for G at position 489 in SEQ ID NO: 5, and the like.

The sixth embodiment of the present invention is DNA comprising the base sequence shown in SEQ ID NO: 3 or 5 which encodes a typical protein of the present invention, mouse or human C16N. Said DNA can be cloned by screening cDNA libraries such as those from human thalamus and the like using C16 DNA shown in SEQ ID NO: 1 in whole or in part as a probe, or by conducting PCR using cDNA prepared from, for example, human brain as templates and using parts of C16 DNA shown in SEQ ID NO: 1 as primers. Alternatively, C16N DNA may also be cloned without using C16 DNA by "expression cloning" described above for the first embodiment of the present invention. The base sequence of C16N DNA cloned can be determined according to the same procedures as those described for C16 DNA.

The seventh embodiment of the present invention is a protein which is encoded by DNA of any one of the third to sixth embodiments of the present invention. Specific examples of such proteins include mouse and human C16N, C16Ns derived from other species, modified proteins of said C16N, and the like. Preparation and determination of the activity of these proteins can be achieved according to the procedures described above for the second and third embodiments of the present invention.

The eighth embodiment of the present invention is a mouse or human C16N, a typical protein of the present invention comprising the amino acid sequence shown in SEQ ID NO: 4 or 6, respectively. C16N is a protein comprising 579 amino acids encoded by the longest open reading frame (the region from position 236 to 1972 in SEQ ID NO: 3 and the region from position 1 to 1737 in SEQ ID NO: 5) of C16N cDNA shown in SEQ ID NO: 3 or 5. These mouse and human C16Ns show an extremely high homology of 99.7% in the amino acid sequences. These proteins can be expressed and purified according to the procedures described above for the second embodiment of the present invention.

The ninth embodiment of the present invention is expression vectors which contain DNA of any one of the first and third to sixth embodiments of the present invention. The tenth embodiment of the present invention is transformants transformed with said expression vector. Furthermore, the eleventh embodiment of the present invention is a process for producing recombinant proteins, said process being characterized in that it comprises culturing said transformant under conditions in which said expression vector can be expressed. Methods for preparation of such expression vectors and transformants or for production of recombinant proteins per se are all well known to those skilled in the art, as described above in connection with the second embodiment of the present invention.

The twelfth embodiment of the present invention is pharmaceutical agents which contain as an active ingredient the protein of the second, seventh, or eighth embodiment of the present invention.

Since the typical proteins of the present invention, C16 and C16N, have the hydroxyapatite-resorbing activity, and activities of supporting survival of neuron, inhibiting proliferation of osteoblast, and promoting expression of type I collagen in osteoblast, they may be useful in the following pharmaceutical applications.

1. Factor for Regulating Calcium Concentration in Blood

Metabolic regulation of the calcium concentration in blood is absolutely essential for survival, and thus quite important. When the blood calcium concentration is decreased for some reason, it causes diseases such as hypocalcemia. In addition, substantial decrease in blood calcium concentration due to, for example, massive hemorrhage or radiation exposure sometimes leads to death.

Since the C16-related proteins of the second, seventh, and eighth embodiments of the present invention have activity of inducing cells which can resorb hydroxyapatite (crystalline calcium in bone) and release calcium, these proteins may be administered as pharmaceutical agents to increase the calcium concentration in blood.

Although the preferred method for such administration to patients is intravenous injection, other routes such as oral administration, use of suppository, subcutaneous injection, intramuscular injection, topical infusion, intraventricular administration, and intraperitoneal administration are also possible. Such dosing may be continued at a dose of about 0.0001–100 mg per day until the symptoms are improved.

2. Neurotrophic Factor

It has been shown in recent years that so-called "neurotrophic factors" act on more various types of neuron than recognized before. As the result, intensive studies about application of neurotrophic factors to various neurological disorders are now in progress. Since the C16-related proteins of the second, seventh, or eighth embodiments of the present invention have activity of supporting survival of neuron, they may be useful, like known neurotrophic factors, as therapeutic agents for diseases such as Parkinson's disease, Huntington's chorea, Alzheimer's disease, and amyotrophic lateral sclerosis.

In addition, the exclusive expression of C16 and C16N of the present invention only in brain and bone suggests that the factors may play an important role as neurotrophic factors in bone, which are involved in the connection between brain and bone, for example, guidance of nerve to bone or survival of neurons in bone. It is therefore expected that these proteins may be quite useful as therapeutic agents for promoting fracture healing when administered as pharmaceutical agents.

These proteins may be administered to patients in the same manner as described in the above section 1. In the case of promotion of fracture healing, C16-related proteins of the present invention which have been incorporated into carriers may be implanted at the site of fracture. Such dosing may be continued at a dose of about 0.0001–100 mg per day until the symptoms are improved.

3. Factor for Promoting Differentiation or Function of Osteoblast

C16 and C16N of the present invention have also activities of inhibiting proliferation of osteoblast and promoting expression of type I collagen in said osteoblast (Examples 14 and 15).

Osteoblast is a cell fated to become osteocyte, and plays major role in bone formation. Type I collagen is one of differentiation markers which is expressed at the early stage of differentiation of osteoblast, and this protein accounts for 90% of bone matrix. It is known that bone formation proceeds via deposition of hydroxyapatite around the fibers of type I collagen secreted from osteoblast.

As described above, C16 and C16N of the present invention have activities of inhibiting proliferation of osteoblast and promoting expression of type I collagen in osteoblast. Thus, these factors are likely to promote differentiation or function of osteoblast by inhibiting proliferation of osteoblast and by promoting expression of type I collagen. It is therefore expected that these proteins may be useful as therapeutic agents for osteoporosis, spinal cord injury, bone fracture, and the like when administered as pharmaceutical agents.

Furthermore, since type I collagen is also expressed in skin and tendon, it is expected that proteins of the present invention which promote expression of type I collagen may be useful as therapeutic agents for disorders of skin or tendon.

Route of administration and dosage of these proteins to patients may be the same as those described in the above section 2.

The thirteenth embodiment of the present invention is partial peptides of C16, C16N or analogous proteins thereof according to the second, seventh, or eighth embodiment of the present invention, comprising at least 6 amino acids or more. The limitation "at least 6 amino acids or more" is based on the fact that a minimal size of polypeptide capable of forming a stable structure is of 6 amino acids, and preferred polypeptides are those comprising about 10–20 amino acids. Examples of such peptide may include those comprising part of C16N and effective in inhibiting the functions of C16N (hydroxyapatite-resorbing activity, activity of supporting survival of neuron, inhibiting proliferation of osteoblast, or promoting expression of type I collagen in osteoblast). Short polypeptides such as those comprising about 10–20 amino acids can be synthesized on peptide synthesizer, while longer polypeptides can be obtained by preparing DNA using the usual genetic engineering techniques(for example, treatments with restriction enzyme (s)), and expressing it in, for example, animal cells. The polypeptide thus prepared can also be modified by conventional methods.

These partial peptides can be useful as pharmaceutical agents as described below and can also be used for production of antibodies.

As described above, such partial peptides include those having inhibitory effect against C16 and C16N activities. As described below in connection with the fifteenth embodiment of the present invention, these inhibitory peptides can be easily selected by adding test materials (i.e., candidates for inhibitory peptides against C16 or C16N activity) to the activity assay systems described above for the third embodiment of the present invention. As described in the seventeenth embodiment of the present invention, such inhibitory peptides can be used as an inhibitor of C16 or C16N activity.

The fourteenth embodiment of the present invention is an antibody against the protein of the second, seventh, or eighth embodiment, or against the partial peptide of the thirteenth embodiment, of the present invention. Such antibodies can be easily prepared by immunizing animals such as rabbit according to the procedures such as those described in "Shin-Saibou-Kougaku-Jikken-Protocol (New Protocols for Experiments in Cellular Engineering)", p. 210, Shujun-Sha (1993). Monoclonal antibodies can also be easily prepared according to the procedures such as those described in "Bunnshi-Seibutugaku-Kennkyu-No-Tameno-Tanpaku-Jikkennhou (Protocols of Protein Experiments for Research in Molecular Biology)", Chapter 4, Youdo-Sha (1994). Such antibodies are useful for affinity chromatography or screening of cDNA library, and as medicines, diagnostic agents or laboratory reagents. Such antibodies include those having neutralizing activity against C16 and C16N. As described below in connection with the fifteenth embodiment of the present invention, these neutralizing antibodies can be easily selected by adding test materials (i.e., candidates for antibodies to C16 or C16N) to the activity assay systems described above for the third embodiment of the present invention. These neutralizing antibodies serve as inhibitors of C16 or C16N activity as described in the seventeenth embodiment of the present invention.

The fifteenth embodiment of the present invention is a screening method for inhibitors of C16 or C16N activity, which method is characterized in that it employs the protein of the second, seventh, or eighth embodiment of the present invention. As used herein, the word "inhibitors of C16 or C16N activity" refers to those which inhibit the activity of C16 and C16N, that is, the hydroxyapatite-resorbing activity, activities of supporting survival of neuron, inhibiting proliferation of osteoblast, or promoting expression of type I collagen in osteoblast.

This screening can be conducted by adding test materials to the activity assay systems described above for the third embodiment of the present invention.

For example, screening of inhibitors of hydroxyapatite-resorbing activity can be performed in the following manner: firstly, bone marrow cell culture in Osteologic well is treated with recombinant C16 or C16N produced in cultured mammal cell expression system such as CHO or COS cells, baculovirus expression system, or *E. coli* expression system to induce cells to become capable of resorbing Osteologic, and the culture is incubated with test materials. The screening for inhibitors of the activity can be achieved by observing whether the pit formation on Osteologic is inhibited.

The sixteenth embodiment of the present invention is inhibitors of C16 or C16N activity obtained by the above screening method of the fifteenth embodiment. Such inhibitors may have any structure and properties, so long as they inhibit activities of C16 or C16N.

The seventeenth embodiment of the present invention is inhibitors of C16 or C16N activity according to the sixteenth embodiment which comprise the partial peptides of the thirteenth embodiment or the antibodies of the fourteenth embodiment of the present invention. Thus, this embodiment is partial peptides or antibodies of the present invention which have effects in terms of inhibiting activities of C16 or C16N. These inhibitors can be easily selected by subjecting test materials (partial peptides or antibodies) to the screening system described above.

The inhibitors of C16 or C16N activity as described above are useful as pharmaceutical agents described below.

Since C16 and C16N of the present invention are supposed to be factors regulating the calcium concentration in blood, their inhibitors may be used as therapeutic agents for diseases resulted from excessive calcium level in blood such as hypertension, arterial sclerosis, diabetes, myocardial infarction, and hypercalcemia.

In addition, C16 and C16N of the present invention are supposed to function as neurotrophic factors, and in particular they are likely to have neurotrophic activity in bone, since they are expressed exclusively in bone and brain. Therefore, their inhibitors may block the nervous system in bone and thereby eliminate the pain associated with bone metastasis in patients with terminal cancer.

These inhibitors may be administered in a similar manner to that described above for the twelfth embodiment of the present invention. Administration may be continued at a dose of about 0.0001–100 mg per day until the symptoms are improved.

The eighteenth embodiment of the present invention is transgenic animals in which DNA of any one of the first and third to sixth embodiments of the present invention has been artificially inserted into their chromosome, or has been deleted from the chromosome, including so-called knockout animals. Since one skilled in the art can easily produce such transgenic animals according to the procedures described in, for example, "Shikkan-Model-Mouse (Disease model mouse)" in *Molecular Medicine* (extra edition, Nakayama-Shoten (1994)), these transgenic animals are also included within the scope of the present invention. The transgenic animals thus produced are quite useful as, for example, model animals for developing pharmaceutical agents, or as animals for screening pharmaceutical agents.

EXAMPLES

Figure 1:
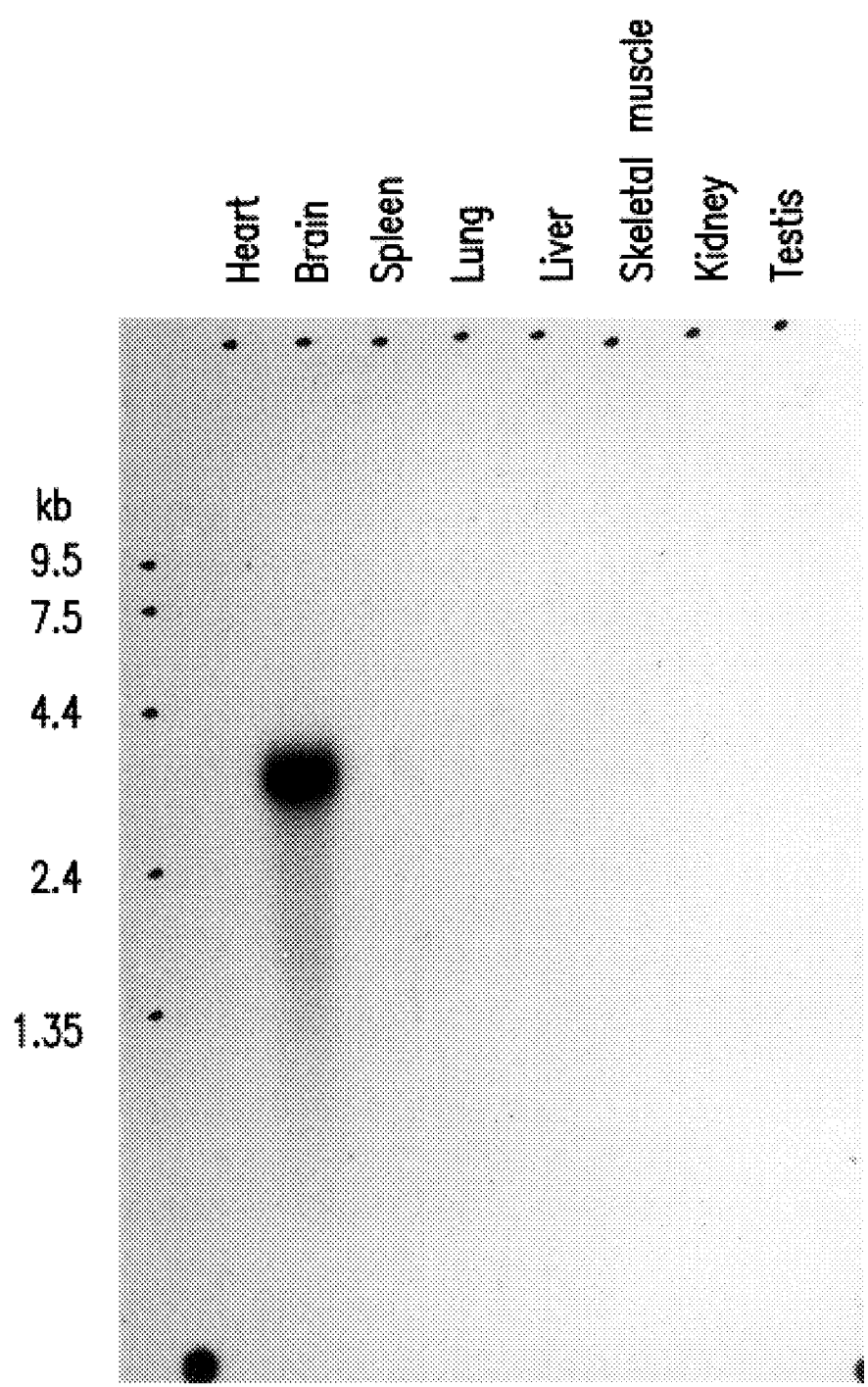
FIG. 1 is electropherogram showing the result of Northern blot analysis in which expression distribution of mRNA corresponding to C16 was evaluated in various mouse tissues.

The present invention is illustrated in detail by the following Examples. The Examples are representative only and should not be construed as limiting in any respect.

Example 1
Construction of Mouse cDNA Library
1.1. Isolation of RNA from Mouse BW5147 Cells
    1.1.1. Isolation of Total RNA
    $1 \times 10^8$ Cells of Mouse BW5147 cell line (ATCC CRL 1588) were treated using AGPC method (acid guanidium thiocyanate-phenol-chloroform method; Tuji, Nakamura, JIKKEN-IGAKU, vol. 9, No. 15, p. 99 (1991)) to isolate total RNA. More specifically, 10 ml of 4 M guanidine isothiocyanate was added to the cell pellet and vigorously shaken immediately. The solution was passed back and forth five times through 18G needle to partially shear the DNA. To this solution, 1 ml of 2M sodium acetate, 10 ml of water-saturated phenol, and 2 ml of chloroform-isoamyl alcohol (49:1) were added sequentially with mixing after each addition. The solution was then vigorously shaken, cooled on ice for 15 minutes, and centrifuged at 10,000 g for 20 minutes at 4° C. The aqueous layer was removed, and thoroughly mixed with an equal volume of isopropanol. The mixture was kept at −20° C. for one hour, and then centrifuged at 10,000 g for 10 minutes at 4° C. After centrifugation, the RNA precipitate was completely dissolved by adding 3 ml of 4 M guanidine thiocyanate. An equal volume of isopropanol was added to the solution, kept at −20° C. for one hour, and then centrifuged at 10,000 g for 15 minutes at 4° C. The supernatant was discarded, and the RNA precipitate was washed with 75% ethanol to obtain total RNA.
    1.1.2. Isolation of mRNA
    Fifteen milligrams of total RNA obtained by repeating the above procedure several times was dissolved in 5 ml of an elution buffer (10 mM Tris-HCl (pH 7.5), 1 mM EDTA, and 0.2% SDS), heated at 65° C. for 2 minutes, and quickly cooled to room temperature immediately. After adding 0.55 ml of 0.5M NaCl, the solution was applied to a column containing 0.5 g of Oligo(dT)-Cellulose (type 7; Pharmacia) equilibrated with a washing buffer (0.5 M NaCl, 10 mM Tris-HCl (pH 7.5), 1 mM EDTA, and 0.2% SDS), and the flow-through fraction was re-applied twice to the column so that mRNA was bound to the column. After washing the column with 15 ml of the washing solution, the RNA bound was eluted with 4 ml of an elution buffer. The eluate was heated at 65° C. for 2 minutes, cooled, adjusted to 0.5 M NaCl, and then re-applied to re-equilibrated column, followed by elution as described above. mRNA was recovered from the eluate by ethanol precipitation, and washed with 75% ethanol.
    1.1.3. Fractionation of mRNA by Sucrose Density Gradient Centrifugation
    Using a density gradient fractionator (Hitachi; DGF-U) and centrifuge tubes treated with diethylpyrocarbonate as well as RNase-free sucrose solutions having different concentrations (5% and 20% (w/v) sucrose), 0.1 M NaCl, 10 mM Tris-HCl (pH 7.5), 1 mM EDTA, and 0.5% SDS, sucrose density gradient was prepared in centrifuge tubes for Beckman SW41Ti using the density gradient fractionator, and left over 2 hours at room temperature to eliminate discontinuity in the gradient. mRNA was then dissolved in 200 µl of TE solution (99% dimethylsulfoxide, 10 mM Tris-HCl (pH 7.5), 1 mM EDTA, and 0.1% SDS), heat-treated at 37° C. for 5 minutes, and then at 65° C. for 10 minutes after addition of 400 µl of 5 mM Tris-HCl (pH 7.5), 1 mM EDTA, 0.5% SDS, to dissociate its non-specific aggregation. After rapid cooling, the mRNA solution was applied onto the sucrose density gradient, and centrifuged at 20,000 rpm for 14 hours at 25° C. in Beckman SW41Ti rotor. After centrifugation, 0.5 ml fractions were collected from the tube using the density gradient fractionator, and ethanol-precipitated. The mRNA precipitate was washed at least three times with 75% ethanol.
    1.1.4. Identification of mRNA
    Aliquots of the mRNA which was fractionated into 50 fractions were injected into Xenopus oocyte, and translated into proteins according to the procedures described below in Example 2.1.3. The supernatant containing the translated product was added to mouse bone marrow cells for assay, and incubated according to the procedures described below in Example 2.2.2 to determine whether or not osteoclast has been generated (that is, to determine which fractions of mRNA contain factors having activity of inducing cells into osteoclast), using TRAP staining described in Example 2.3.1. As a result, activity peaks were observed in Fractions 27 and 32.
1.2. Preparation of cDNA Library
    Fractions 27–33 containing activity peaks were pooled as an active fraction, and cDNA library was prepared from this active fraction using a modified method of Gubler & Hoffman (*Gene*, 25, p. 263 (1983)). More specifically, using 2 µg mRNA of the active fraction, the first stand was synthesized by M-MuLV reverse transcriptase using oligo-dT primer having Xho I site. The second strand was then synthesized using DNA polymerase I, ligated to EcoRI adapter, and digested with XhoI. The adapter and primer were then removed by gel filtration (Sephacryl Spin Column; Pharmacia). The above cDNA synthesis was conducted using ZAP cDNA Synthesis Kit (Stratagene) and SUPER-SCRIPT II reverse transcriptase (BRL).
    Next, EcoRI/XhoI-cut ZAP Express™ vector was ligated to the cDNA prepared above, packaged using Gigapack II Gold packing extract (mcrA⁻, mcrB⁻, mmr⁻; Stratagene), and *E. coli* strain PLK-F' was infected with the packaged phage. As a result, cDNA library comprising $6.3 \times 10^5$ independent clones having an average length of 2.26 kb was obtained.

Example 2
Expression Cloning

SUMMARY cDNA library prepared in 1.2 was divided into 63 pools of 10,000 clones/pool, and cRNAs from each pool were injected into Xenopus oocyte using the procedures described below in 2.1.2–2.1.3 so that they are translated into proteins. According to the procedures described below in 2.2.2, the culture supernatant containing the translated products was added to mouse bone marrow cells for assay. Each assay described below was conducted, and the pools which were judged positive were selected. The positive pool was further divided into 10 subpools, and cRNAs were prepared therefrom in the same manner. The cRNAs were then expressed in oocyte, and the activity was measured to select positive pools. These steps were repeated until a single clone was obtained.

In the first screening, TRAP staining described below in 2.3.1 was used for judgment of differentiation-induction activity into osteoclast, and 3 positive pools were selected from 63 pools. In the second and subsequent screenings, three positive pools were each divided into 10 subpools (1000 clones/pool), and those which exhibited positive reactions in all of the three different assays (TRAP staining in 2.3.1, the pit formation assay using dentine slice in 2.3.2, and the pit formation assay using Osteologic well in 2.3.3, all described below) were selected.

In the second screening, three pools were selected by the order of strength of their positive reactions, and each of these three pools was further divided into 10 subpools (200 clones/pool) which were then subjected to the third screening. In the third screening, three positive pools were selected by the order of strength of their positive reactions, and each of these pools was divided into 10 subpools (24 clones/pool) which were further subjected to the fourth screening. In this screening, the subpools were separated into two groups: (i) those which were positive in all of the three assays, and (ii) those which were positive only in the pit formation assay using Osteologic well, but not in other assays. From those subpools classified into the group (ii), which were positive only in regard of the pit formation activity on Osteologic well, two pools were selected by the order of strength of their activities, and they were singly cloned. The single clones were then subjected to the fifth screening, and eight clones were selected as positive clones by the order of their activities. These eight clones were subjected to the calcitonin receptor-detecting assay of 2.3.4 in addition to the above three assays, and one of the clones which exhibited positive reaction only in the pit formation assay using Osteologic well was designated as C16. The results of the assays for C16 are shown below in the "RESULT" sections.

2.1. Preparation of Samples for Assay 2.1.1. Preparation of DNA

E. coli XL1-Blue was infected with $1 \times 10^4$ pfu of lambda phages from each pool, plated on 15 cm dish to generate plaques. To this plate, 13 ml of SM buffer was added to prepare plate lysate. To this plate lysate, DE52 (DEAE-cellulose; Whatman) was added to bind to substances other than phage DNA. To the supernatant obtained by centrifugation, DE52 was added again, and the phage DNA contained in its supernatant was recovered. This DNA was extracted once with phenol and phenol-chloroform (1:1), and recovered by ethanol precipitation. The phage DNA thus prepared was cut with NotI restriction enzyme, and 1/50 volume thereof was electrophoresed on 1% agarose for quantification.

2.1.2. Synthesis of cRNA

In order to prepare template DNA, at least 1 $\mu$g of the phage DNA from each pool prepared in 2.1.1 was treated with proteinase K (Stratagene) at 37° C. for one hour, and after treating with phenol-chloroform, template DNA was recovered by ethanol precipitation. This DNA was used to synthesize cRNAs according to mRNA capping kit (Stratagene). The cRNAs were recovered by subjecting them to phenol-chloroform treatment and ethanol precipitation, and 1/10 volume thereof was used for quantification by 1% agarose-gel electrophoresis. The cRNAs were then adjusted to 1 $\mu$g/$\mu$l for use in microinjection.

2.1.3. Expression by Xenopus Oocyte

Oocyte mass was removed from female Xenopus having body length of about 10 cm, and transferred to dishes containing MBS ($Ca^{2+}$; 88.0 mM NaCl, 1.0 mM KCl, 2.4 mM $NaSO_3$, 0.3 mM $Ca(NO_3)_2.4H_2O$, 0.41 mM $CaCl_2.4H_2O$, 0.82 mM $MgSO_4.7H_2O$, 10 $\mu$g/ml penicillin, 10 $\mu$g/ml streptomycin, 50 U/ml nystatin, 15 mM Tris-HCl (pH 7.6)). The oocyte cells were then separated from each other under stereoscopic microscope using precision scissors and forceps, and intact living cells at stage V or VI were selected. Into these oocytes, 50 nl/oocyte of cRNAs was injected from capillary using 10 $\mu$l digital micro-dispenser (Drummond). After removing cells that were dead or damaged, they were incubated in MBS containing 2% FCS for 3 days at 20° C. The supernatant was centrifuged, and filtered through 0.22 $\mu$m filter in order to remove debris and to sterilize. The supernatant was then used as sample for the assays.

2.2. Assays 2.2.1. Preparation of Mouse Bone Marrow Cells

From 6–12 week-old mouse (C3H/HeJ; Nihon Crea), femur and shank were aseptically removed, and their epiphyses were cut off. Bone marrow cells were extruded once from both ends with 1 ml of $\alpha$-MEM medium (containing 10% fetal bovine serum, 100 U/ml penicillin G, 100 $\mu$g/ml streptomycin) using a syringe equipped with 26G needle. After pipetting thoroughly and allowing the bone debris to precipitate, the supernatant was recovered. The cells were further washed once or twice with fresh medium to obtain bone marrow cells for the assays.

2.2.2. Method for Inducing Cells into Osteoclast

The bone marrow cells prepared above were suspended in $\alpha$-MEM medium containing $10^{-8}$ M active form of vitamin D $[1,25(OH)_2D_3]$, and adjusted to $2 \times 10^6$ cells/ml. Each 180 $\mu$l aliquot was then introduced into 96-well plate together with 20 $\mu$l of the assay sample prepared in 2.1.3, and incubated at 37° C. under 5% $CO_2$ for one to two weeks. During the incubation, ¾ volumes of the medium were replaced with a flesh medium, and the same volume of the assay sample was newly added, at intervals of 3–4 days.

2.3. Method for Identification of Osteoclast 2.3.1. TRAP Staining

TRAP (Tartarate Resistant Acid Phosphatase) which is a marker enzyme for osteoclast was stained with its substrate. More specifically, the cultured bone marrow cells of 2.2.2 were fixed with acetone-citrate buffer, and then reacted with the substrate (Naphthol AS-MX phosphate) and dye (Fastredviolet LB salt) in the presence of tartarate at 37° C. for one hour to stain the cells (Takahashi et al., Endocrinology, 122, p. 1373 (1988)).

RESULT

C16 was judged negative by comparison with the TRAP staining of positive control in which bone marrow cells were treated with IL-1$\beta$ (50 ng/ml) or LIF (25 U/ml), known factors which induce bone marrow cells to become osteoclast, to differentiate them to become osteoclast.

2.3.2. Pit Formation Assay Using Dentine Slices

Dentine slices having 6 mm diameter and 1 mm thickness were prepared from ivory, and sterilized by ultrasonication in 80% alcohol. After washing with $\alpha$-MEM medium, each slice was transferred to the bottom of well in 96-well plate, and on that slice, differentiation of bone marrow cells into osteoclast was induced according to the procedure of 2.2.2. After 1 to 2 weeks, osteoclasts on the dentine slice were stained with TRAP staining method of 2.3.1, treated overnight with 0.25% trypsin-0.02% EDTA, and then scraped off with silicone scraper. Pits (resorption cavities) on the slice were observed under microscope, and the number of pits or the number of meshes per pit was determined to evaluate the bone resorbing activity (bone resorbing activity) of differentiated cells induced from bone marrow cells.

RESULT

The number of pits on dentine slice generated by cells induced with C16 was very small and it was 1/10–1/5 of that observed with LIF (25 U/ml).

2.3.3. Pit Formation Assay Using Osteologic Well

According to the procedure of 2.2.2, differentiation of bone marrow cells into osteoclasts was induced in wells coated with hydroxyapatite (trade name: Osteologic; MILLENIUM BIOLOGIX). After one week, the cells were removed by treatment with 20% sodium hypochlorite for 5 minutes, and the number of pits on the well was calculated as the number of meshes per pit to determine the bone resorbing activity (bone resorbing activity) of differentiated cells induced from bone marrow cells.

RESULT

The number of pits on Osteologic well has an average of 80–90 per well for the cells generated by C16. C16 was therefore judged positive for the pit forming activity, since the observed number was larger than that observed in negative control (15–20 pits on the average) in which distilled water instead of cRNA was introduced into Xenopus oocyte and the culture supernatant was added to bone marrow cells, and the number was also larger than that observed with LIF (25 U/ml) as a positive control (50 pits).

2.3.4. Detection of Calcitonin Receptor

Using chamber slides (LaboTec), differentiation of bone marrow cells into osteoclast was induced by the method of 2.2.2. To the cells, 200 μl of 0.2 μCi/ml [$^{125}$I]-salmon calcitonin was then added and reacted at 37° C. for one hour. The reaction was stopped by removing the reaction solution and washing three times with PBS. The cells was then fixed with 2.5% glutaraldehyde, and TRAP-stained according to the procedure of 2.3.1. The slide glass was detached from the chamber, and air-dried well. In the dark room, the slide was then soaked briefly in emulsion (Kodak NTB-2), and after excessive emulsion was removed, kept at 4° C. for 2–7 days in a dark box. The slide was then developed in the usual manner, air-dried, and observed under microscope.

RESULT

The cells generated by C16 was judged not to have calcitonin receptors because few dense particles were observed on the autoradiogram of that cells.

CONCLUSION

Since C16 was positive only in the pit formation assay using Osteologic well but not in other assays described above, the cells induced by C16 are judged to be cells other than osteoclast and having hydroxyapatite-resorbing activity.

Example 3

Method for Identifying Macrophage

Although the cell induced by C16 proved not to be osteoclast, there was another possibility that it was macrophage, since Davies, J. E. et al., ASBMR Poster Presentation C122 (1994) has reported that in addition to osteoclast, macrophage can also degrade Osteologic well to form pits. We therefore conduced the following experiments to determine whether or not the cell induced by C16 was macrophage.

3.1. Double Staining with α-naphthyl Butyrate Esterase and Naphthol-AS-D-chloroacetate Esterase The culture medium for differentiated cells on chamber slide or plate which were generated according to the procedure of 2.2.2 was removed, washed with PBS, and dried. The cells were fixed with a fixing solution (see below) at 4° C. for 30 seconds, and then washed with water and dried. Next, the cells were stained by treating with esterase reaction solution I (see below) for 30 minutes at room temperature. After washing with water, the cells were further stained by the treatment with esterase reaction solution II (see below) for 30 minutes at room temperature. After washing with water, the cells were stained with a counterstaining solution (see below) for 2 minutes, washed with water, dried, and observed under microscope.

(i) Fixing Solution: Buffered Formalin-acetone Solution (pH 6.6)

| Composition: | | |
|---|---|---|
| | Na$_2$HPO$_4$ | 20 mg |
| | KH$_2$PO$_4$ | 100 mg |
| | distilled water | 30 ml |
| | acetone | 45 ml |
| | formalin | 25 ml |

(ii) Esterase Reaction Solution I

| Solution A: | 1/15 M phosphate buffer (pH 6.3) | 9.5 ml |
|---|---|---|
| | Fast Garnet GBC salt | 10 mg |
| Solution B: | α-naphthyl butyrate | 10 mg |
| | ethylene glycol monomethyl ether | 0.5 ml |

Mix solution A with B, and filtrate through membrane filter.

(iii) Esterase Reaction Solution II (prepare just before use)

| Solution A: | 1/15 M phosphate buffer (pH 7.4) | 9.5 ml |
|---|---|---|
| | Fast Blue RR salt | 5 mg |
| Solution B: | naphthol-AS-D-chloroacetate | 1 mg |
| | N,N-dimethylformamide | 0.5 ml |

Mix solution A with B, and filtrate through membrane filter.

(iv) Counterstaining Solution: 1% Methyl Green Staining Solution

| Composition: | | |
|---|---|---|
| | sodium acetate.H$_2$O | 1.09 g |
| | barbital sodium | 1.65 g |
| | 0.1N HCl | 120 ml |
| | distilled water | 80 ml |
| | methyl green | 4 g |

Adjust the total volume to 400 ml, and filtrate.

RESULT

Unlike the positive control, i.e., mouse peritoneal macrophage, the cells generated by C16 were not stained reddish brown.

3.2. Fluorescent Antibody Staining with Mac1 and F4/80 Antibodies

From differentiated cells on chamber slide or plate which were generated according to the procedure of 2.2.2, the culture medium was removed, and replaced with a fresh medium. Mac1 (PHARMINGEN) or F4/80 (CALTAG LABORATORIES) antibody was then added to the cells, and incubated for one hour at 37° C. under 5% CO$_2$. After removing the medium, the cells were washed several times with PBS, and then fixed with 3.7% formalin-PBS for 5 minutes at room temperature. Then, the cells were washed several times with PBS, dried, and observed under microscope.

RESULT

Unlike the positive control, i.e., mouse peritoneal macrophage, the cells generated by C16 were not stained with either antibody.

3.3. Phagocytic Activity on Fluorescent Latex Beads

Suspension of fluorescent latex beads (particle size, 0.75 μm: Polysciences) was 100-fold diluted in RPMI 1640 medium supplemented with 10% FBS, and added in an appropriate amount to the cells in 96-well culture plate. After incubating for one to several hours at 37° C. under 5% $CO_2$ in an incubator, the medium was removed, and the cells were washed several times with PBS, and fixed with 3.7% formalin-PBS for 5 minutes at room temperature. The cells were washed again several times with PBS, dried, and observed under microscope to measure phagocytes.

RESULT

Cells which phagocytosed 20 latex beads or more were considered as phagocytes. Most of the cells generated by C16 phagocytosed as few as about 5 latex beads, whereas more than 80% of peritoneal macrophages (positive control), were phagocytes.

CONCLUSION

In any of the above three assays, the differentiated cells induced by C16 were not judged as macrophage.

Example 4

Conversion of Recombinant Phage DNA into Phagemid DNA

Inserted DNA in ZAP Express vector can be subcloned into pBK-CMV by its in vivo excision. XL1-Blue MRF' *E. coli* strain was infected with ZAP Express phage and ExAssist helper phage to produce pBK-CMV phagemid, and then heat-treated to death. Next, XLOLR *E. coli* strain was infected with the phagemid. To the strain, a medium was added, incubated for 45 minutes, plated onto LB plates, and further incubated.

Example 5

Preparation of Plasmid DNA

Positive colonies were picked up with toothpicks, incubated overnight in 2 ml LB (100 μg/ml ampicillin), and used for plasmid preparation by alkaline-SDS method. The plasmid DNA obtained was cleaved with appropriate restriction enzymes, and electrophoresed on 1% agarose gel to confirm the insertion of C16 cDNA in the vector.

Example 6

Base Sequencing of C16 cDNA

Determination of the base sequence of C16 cDNA obtained in Example 5 was achieved using dideoxy method developed by Sanger et al. (Auto Read Sequencing kit, Pharmacia Biotech).

The base sequencing revealed that the cDNA comprised 2911 bp shown in SEQ ID NO: 1. The deduced amino acid sequence shown in SEQ ID NO: 2 was also obtained from the longest open reading frame of the cDNA.

Example 7

Expression Analysis of Gene Corresponding to C16 by Northern Blotting

Total RNA was prepared from various mouse tissues, including bone, bone marrow cells, muscle, and the like, according to 1.1.1. Then, 10–20 μg of total RNA was dissolved in a sample buffer, denatured by heating at 65° C. for 5 minutes, electrophoresed on 6% formaldehyde agarose gel, and then transferred onto nylon filter (Hybond N$^+$; Amersham) MTN blots membrane on which poly A$^+$ RNA derived from various tissues has been preblotted (Clontech) was also used. As a probe, the full-length C16 cDNA (about 3 kbp) labeled with $^{32}P$ was used.

The probe was hybridized to RNAs fixed on filter in 50% (v/v) formaldehyde/5×SSC/5×Denhardt's/1% (w/v) SDS/ 0.01% (w/v) denatured salmon sperm DNA at 42° C., washed in 2×SSC/0.1% SDS at 50° C., and then in 0.1% SSC/0.1% SDS at 50° C. After draining off the liquid, the filter was subjected to autoradiography for 1–3 days at −80° C. The autoradiography was conducted using Kodak SB5 or Fuji AIFRX X-ray film together with intensifying screen.

RESULTS

Figure 2:
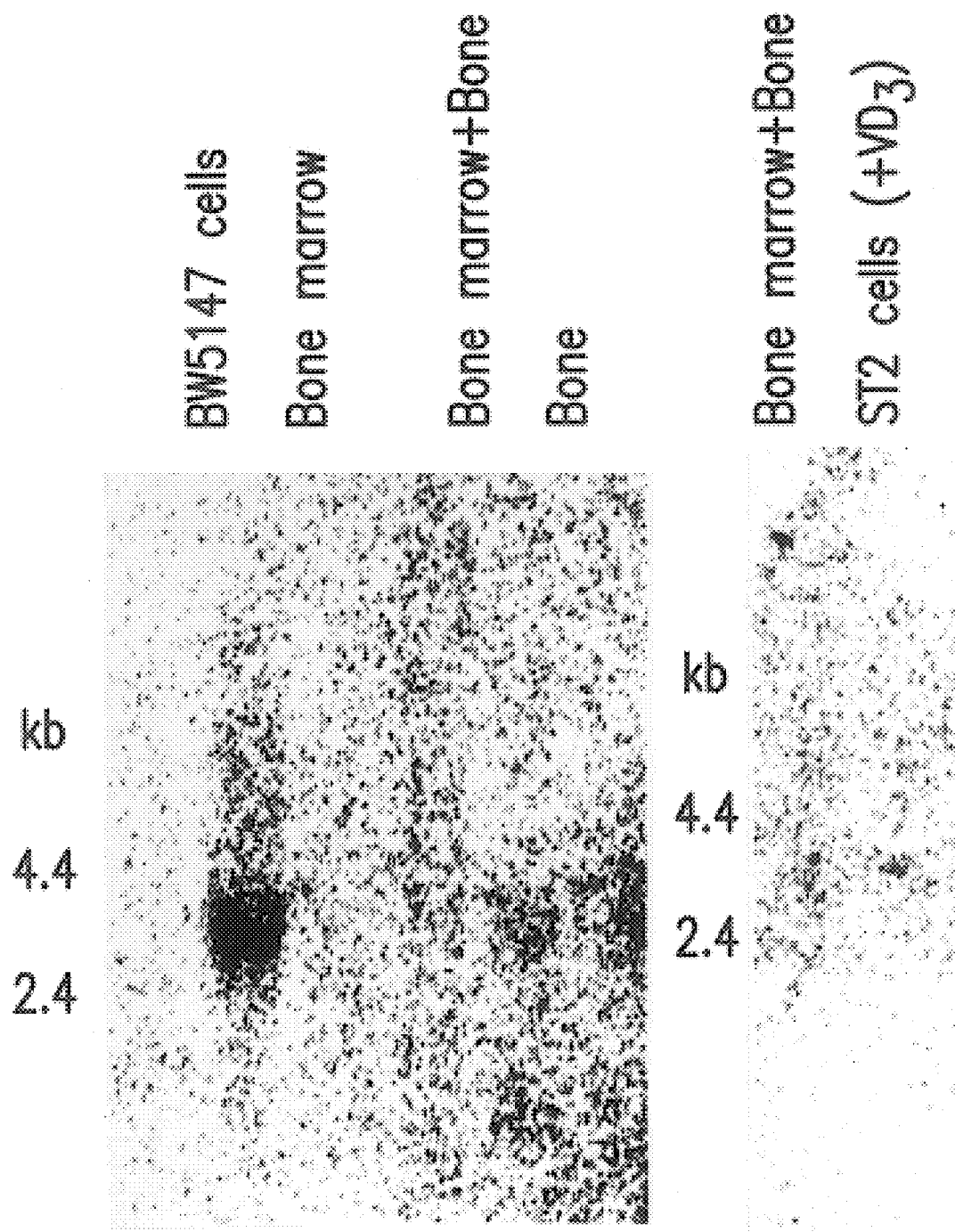
FIG. 2 is electropherogram showing the result of Northern blot analysis in which expression distribution of mRNA corresponding to C16 was evaluated in BW5147 cells, bone marrow cells, bone, and osteoblast-like cell line (ST2).
Figure 3:
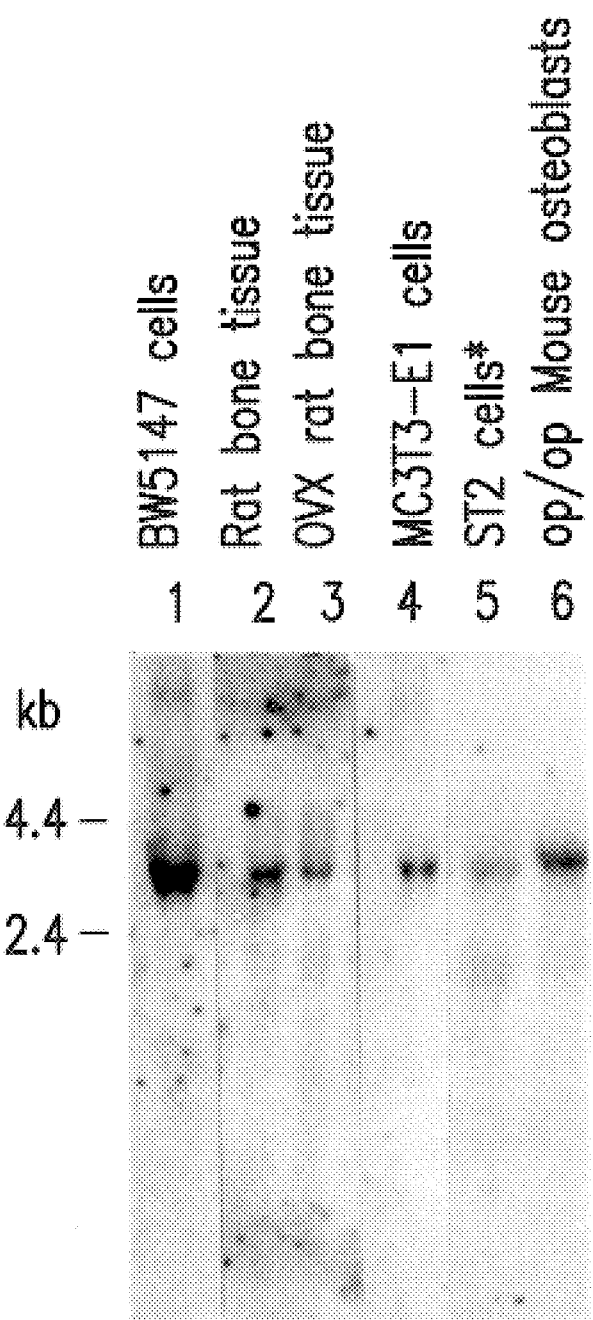
FIG. 3 is electropherogram showing the result of Northern blot analysis in which expression distribution of mRNA corresponding to C16 was evaluated in BW5147 cells, bone tissue, osteoblast-like cell line, and primary culture of osteoblast.

The result of Northern blotting of various mouse tissues (each 2 μg mRNA) is shown in FIG. 1. When C16 was used as probe, mRNA band was exclusively expressed only in brain, but never detected in other tissues. FIG. 2 shows the result of similar Northern blotting in which each 10 μg of total RNA from BW5147 cells, bone marrow cells, bone, and osteoblast-like cell line (ST2) was used. In addition, FIG. 3 shows the result of similar Northern blotting in which each 10 μg of total RNA from BW5147 cells, bone tissue, osteoblast-like cell lines (ST2, MC3T3-E1), and primary osteoblast culture was used. When C16 was used as a probe, mRNA bands were detected in the samples from BW5147 cells, bone marrow cells+bone, bone tissue, primary osteoblast culture, and osteoblast-like cell lines (ST2, MC3T3-E1), but not in the sample from bone marrow cells. This observation indicated that the mRNA was expressed in BW5147 cells, bone tissue, osteoblast-like cell lines (ST2, MC3T3-E1), and primary osteoblast culture.

Figure 4:
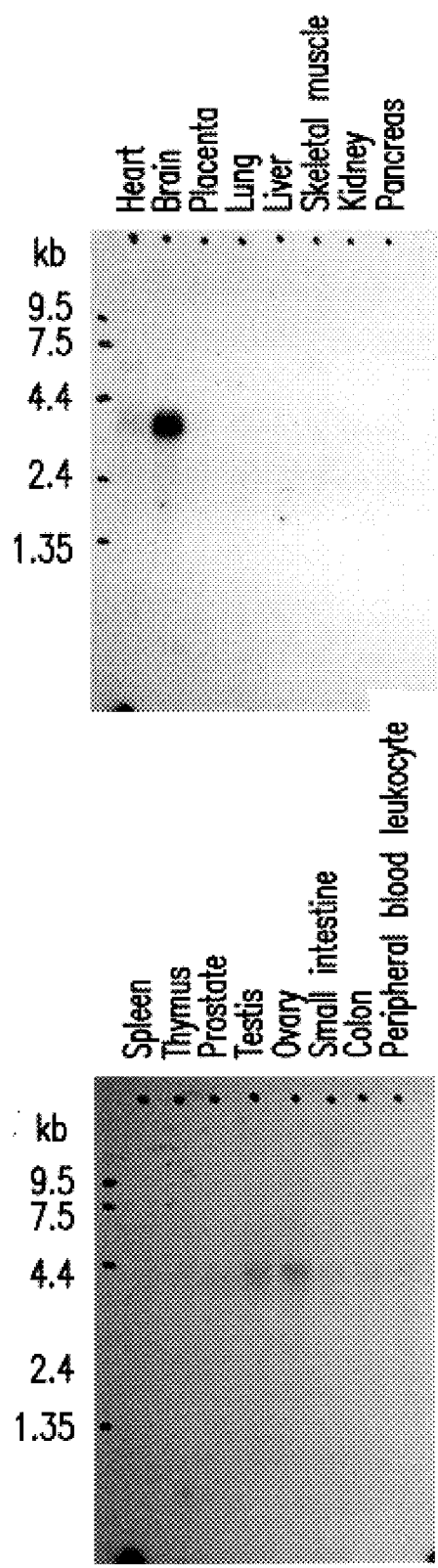
FIG. 4 is electropherogram showing the result of Northern blot analysis in which expression distribution of mRNA corresponding to C16 was evaluated in various human tissues.
Figure 5:
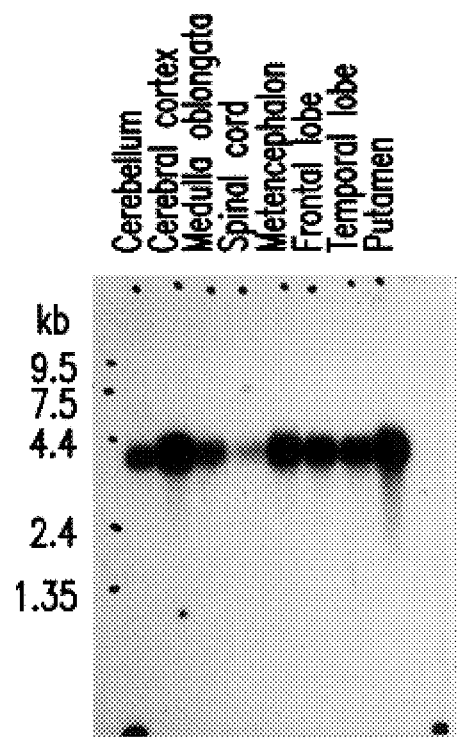
FIG. 5 is electropherogram showing the result of Northern blot analysis in which expression distribution of mRNA corresponding to C16 was evaluated in various tissues of human brain.
Figure 5:
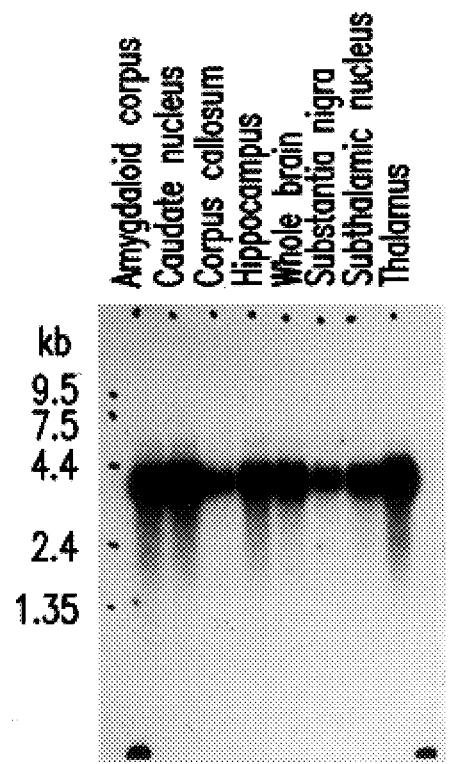

FIG. 4 shows the result of Northern blotting in which the tissue-specificity was analyzed in various human tissues (each 2 μg mRNA) using mouse C16 cDNA as a probe. It was found that the mRNA was abundantly and predominantly expressed in brain, although it was also expressed in some degree in heart, testis, and ovary. Thus, FIGS. 1 and 4 suggest that the mRNA exhibits essentially the same tissue-specificity in mouse and human tissues. FIG. 5 shows the result of Northern blotting for various tissues in human brain (2 μg mRNA). Although the mRNA was expressed in all of the brain tissues studied, the amount was least in spinal cord, medulla oblongata, and cerebellum, and was high in putamen, caudate nucleus, and thalamus.

Figure 6:
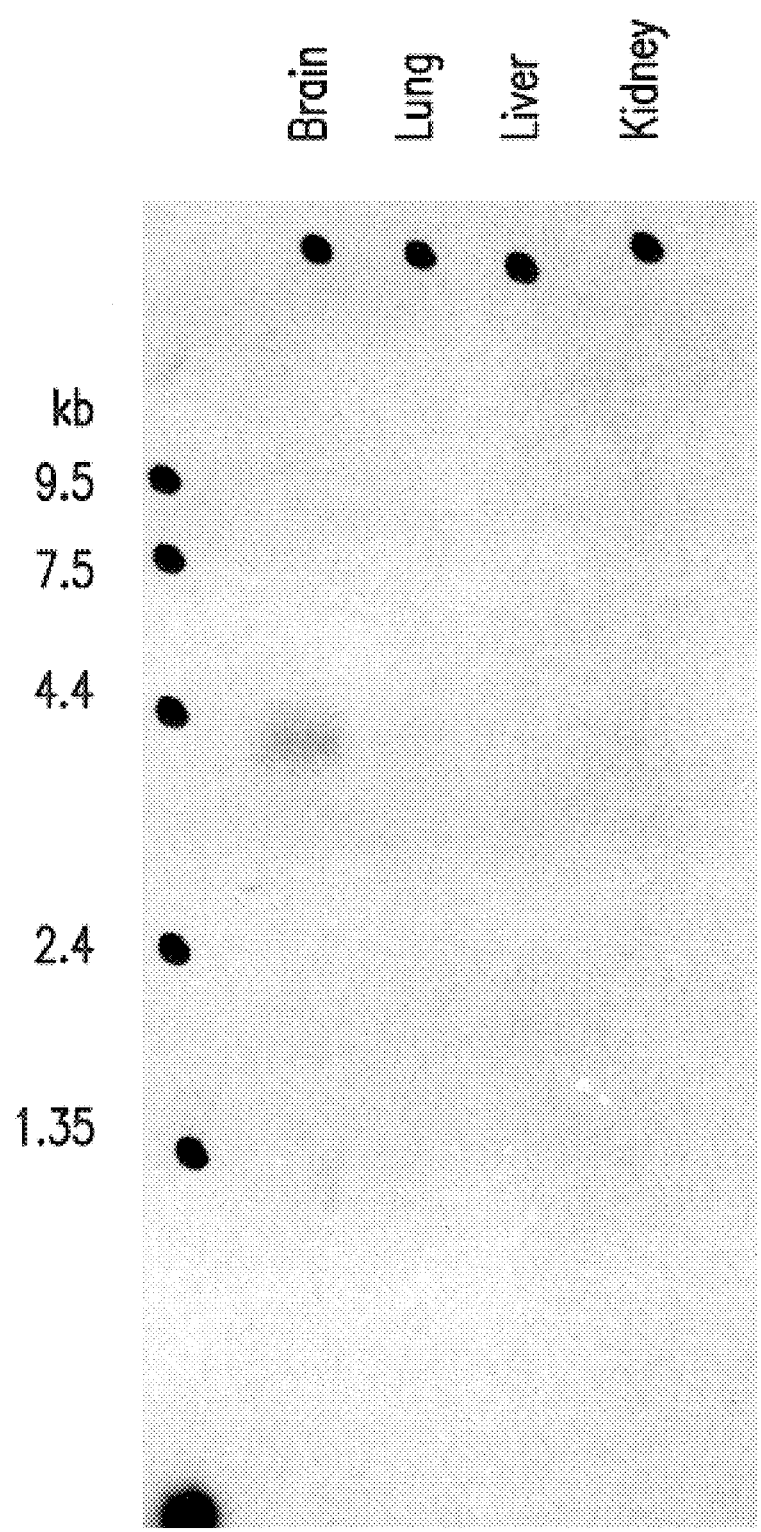
FIG. 6 is electropherogram showing the result of Northern blot analysis in which expression distribution of mRNA corresponding to C16 was evaluated in various tissues of human fetus.
Figure 7:
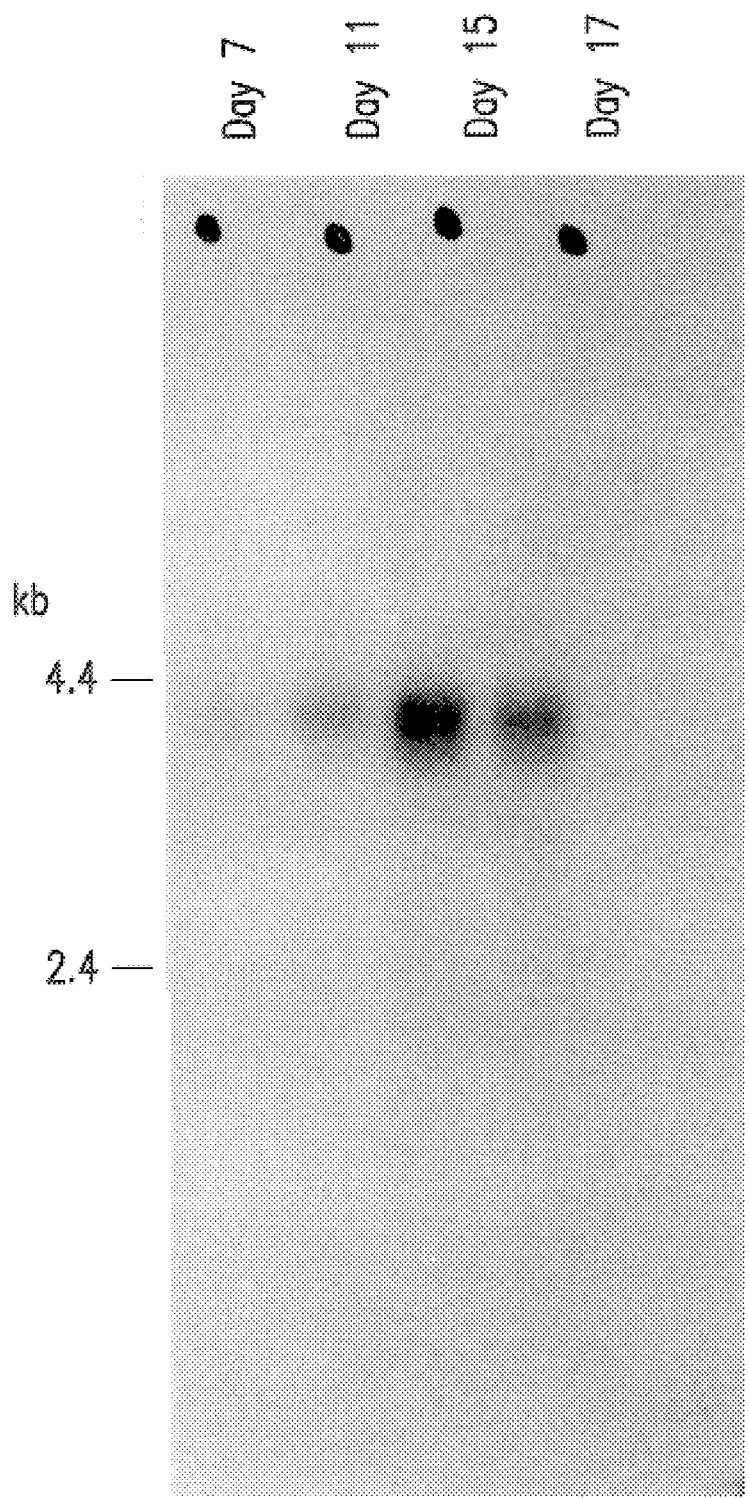
FIG. 7 is electropherogram showing the result of Northern blot analysis in which expression distribution of mRNA corresponding to C16 during embryogenesis of mouse was evaluated.

FIG. 6 shows the result of Northern blotting for various tissues in human fetus (2 μg mRNA), indicating that the mRNA was also expressed exclusively only in brain. FIG. 7 shows the result of expression in mouse embryos at embryonic-day 7 to 17 (2 μg mRNA), indicating that the expression began at embryonic-day 7, reached the peak at embryonic-day 15, and decreased somewhat at embryonic-day 17. The results shown in FIGS. 6 and 7 indicate that the expression of mRNA detectable with C16 cDNA probe begins at an early stage of the development, and becomes exclusive only in brain even in embryonal period. Similarly, the results in FIGS. 1–5 indicate that the mRNA is expressed exclusively in brain and bone among the tissues studied.

Example 8

Expression Analysis of Gene Corresponding to C16 by RT-PCR

Based on total RNA (1 μg) prepared from various cells and tissues, double-stranded DNA was firstly synthesized, and used as template in PCR reaction, according to RT-PCR kit (PERKIN ELMER). Sequences of primers synthesized for this gene amplification were 5'-ATCCTTAGCACATTCCTTAC-3' (SEQ ID NO: 7)for 5'-primer and 5'-AGAAACTTGCTCCCAGAGCT-3' (SEQ ID NO: 8)for 3'-primer. The size of DNA fragment amplified with these primers are 526 base pairs. As a control, G3PDH (glyceraldehyde-3-phosphate dehydrogenase) primers (having the sequences: 5'-TGAAGGTCGGTGTGAACGGATTTGGC-3' (SEQ ID NO: 9)for 5'-primer and 5'-CATGTAGGCCATGAGGTCCACCAC-3' (SEQ ID NO:

10)for 3'-primer, and amplifying DNA fragment of 983 base pairs) were used. The reaction conditions used such as composition of the reaction mixture were as those of standard procedure, and the reaction was conducted 30–40 cycles in DNA thermal cycler under the conditions of denaturation at 94° C. for one minute, annealing at 60° C. for one minute, and strand-elongation at 72° C. for two minutes. A tenth part of the reaction mixture was electrophoresed on 1% agarose gel to check the band.

RESULT

Figure 8:
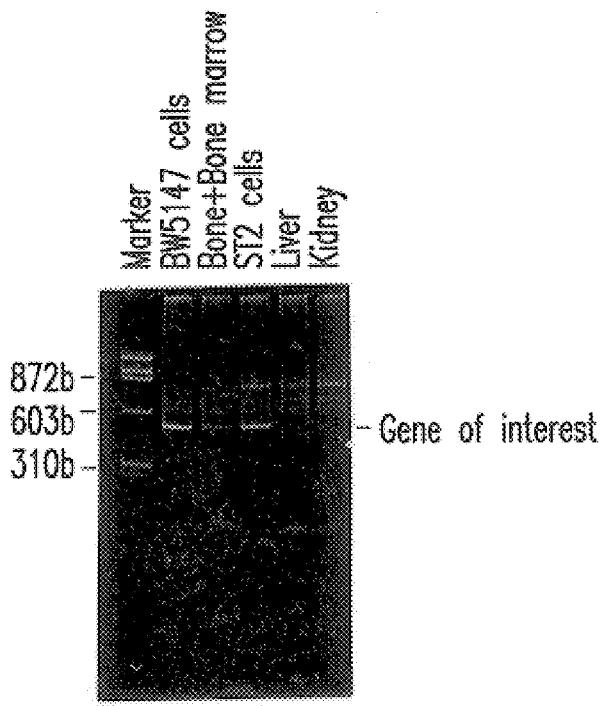
FIG. 8 is electropherogram showing expression distribution of mRNA corresponding to C16 in BW5147 cells, bone plus bone marrow, ST2 cells, liver, and kidney, evaluated by RT-PCR.
Figure 8:
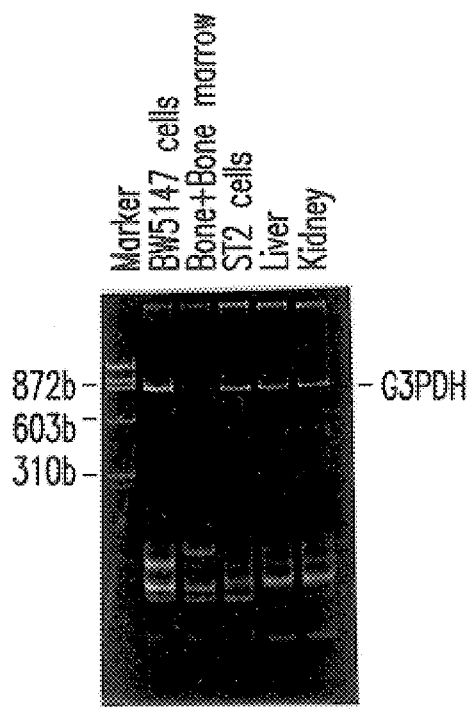

FIG. 8 shows the result of the above reactions using 1 µg of total RNA from various tissues as templates. The expression was detected in BW5147 cells, bone marrow cells+ bone, and ST2 cells, but not in liver and kidney. This result is consistent with that of Northern blotting shown in FIG. 2. The same RNAs were also used in the control RT-PCR for G3PDH to provide information about appropriate amount of RNA and degree of separation.

Example 9

Expression of C16 Gene in Mammal Cell Culture

C16 cDNA obtained in Example 2 was subcloned into pBK-CMV vector, and used to transform *E. coli* strain JM109. DNA was prepared by alkaline-SDS method, and purified by ultracentrifugation twice. The purified DNA was used to transfect COS-7 cells using LIPOFECTAMINE (GIBCO BRL). The cells were then incubated in serum-free medium for 5 days, and the culture supernatant was recovered as C16 protein preparation.

Figure 9:
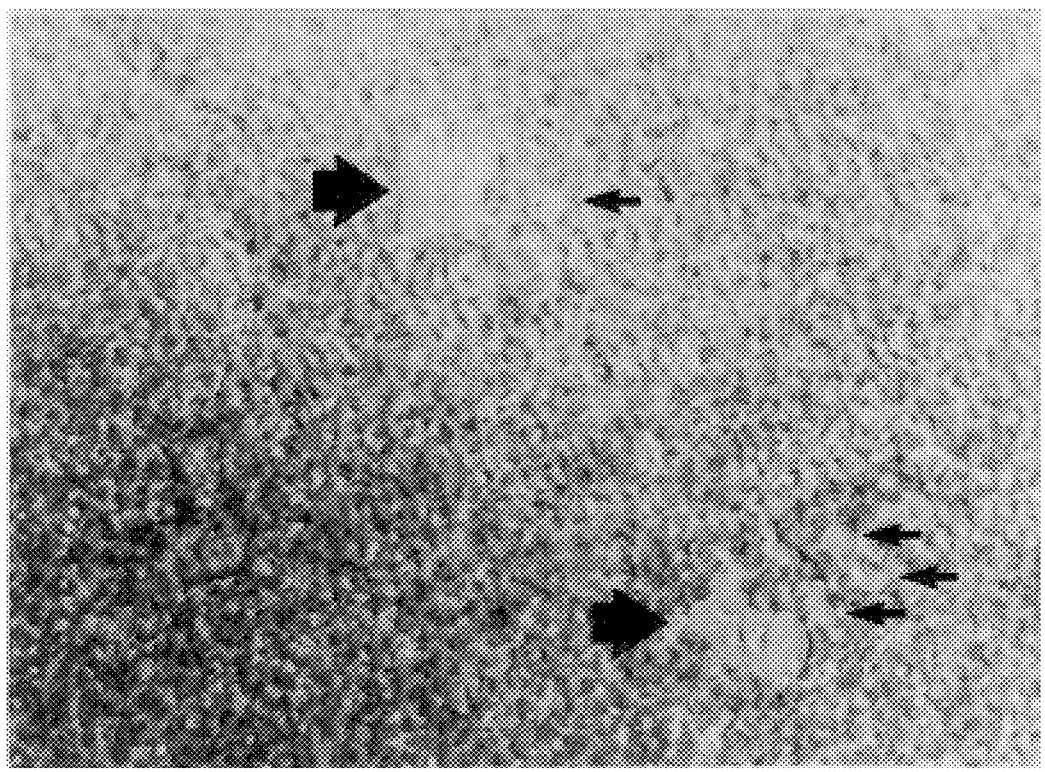
FIG. 9 is microphotograph showing the result of experiments in which culture supernatant from COS-7 cells transfected with C16 cDNA was added to bone marrow cells in Osteologic well to evaluate the pit formation activity. Major pits are indicated by arrowheads.
Figure 10:
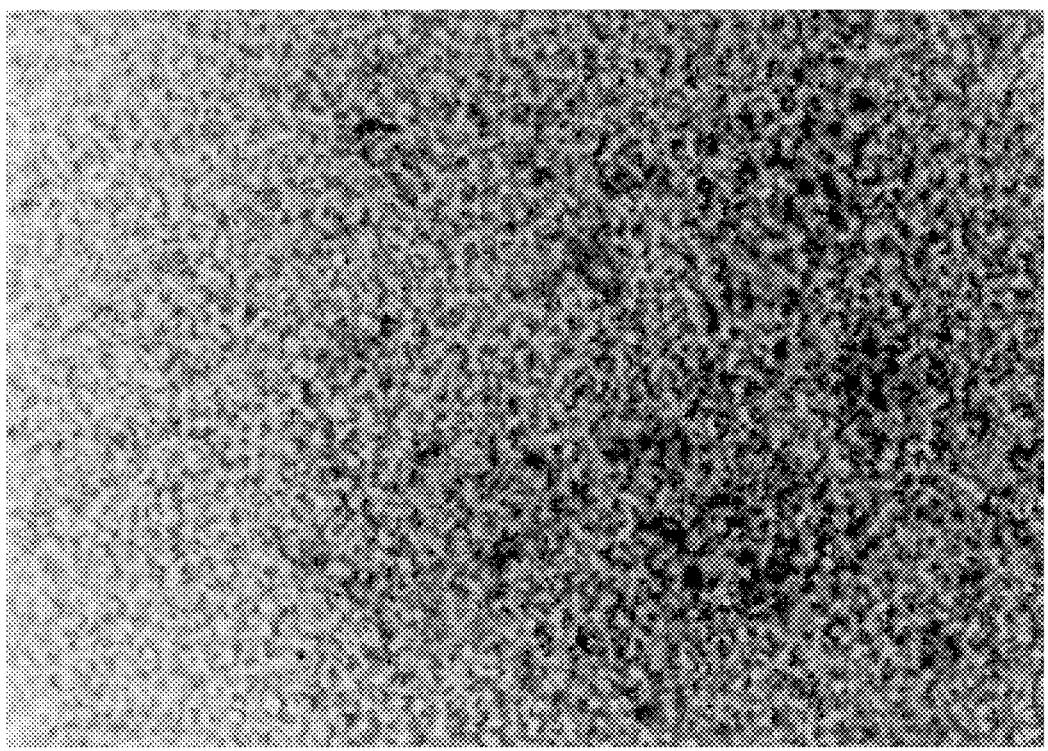
FIG. 10 is microphotograph showing the result of control experiment in which culture supernatant from COS-7 cells transfected with vector DNA containing no C16 DNA was added to bone marrow cells in Osteologic well to evaluate the pit formation activity.

Activity of the culture supernatant was confirmed on the basis of its pit formation activity on Osteologic well measured according to 3.2.2. As shown in FIG. 9, addition of the culture supernatant from C16 cDNA-transfected cells induced formation of pits (major pits are shown by arrowheads). The number of pits was 16 pits/well on the average. When the culture supernatant from COS-7 cells transfected with only a vector which does not contain any insert DNAs was added to bone marrow cells, no pits were detected as shown in FIG. 10. These results confirmed the expression of C16 by COS-7 cells.

Example 10

Cloning of Mouse and Human C16N Gene

Mouse whole brain cDNA library (CLONTECH) was screened for genes analogous to C16 gene. About 3 kbp full-length mouse cDNA was labeled with $^{32}$P by random priming (BCABEST labeling kit, TAKARA), and used as a probe to screen 500,000 plaques of cDNA library by hybridization. Hybridization was conducted overnight in a buffer containing 50% formamide, 5×SSC, 1×Denhardt's solution, 25 mM NaPO$_4$ (pH 6.8), and 50 µg/ml denatured salmon sperm DNA at 42° C. Filter was washed twice in 2×SSC, 0.1% SDS at 55° C. for 10 minutes, and then in 0.5×SSC, 0.1% SDS at 55° C. for 30 minutes. Positive clone obtained in the screening was separated, and the base sequence was determined in the usual manner. As a result, cDNA comprising 3065 bp shown in SEQ ID NO: 3 was obtained. The longest open reading frame of the cDNA encodes the deduced amino acid sequence comprising 579 amino acids shown in SEQ ID NO: 4. When compared to C16, the amino acid sequence of this novel protein comprises the region from position 1 to 245 of the amino acid sequence of C16 shown in SEQ ID NO: 2, and additional 334 amino acids linked to its C-terminus. Since the novel protein proved to be a factor having similar structure to that of C16, it was named "C16N".

Next, we cloned the gene for human C16N. Specifically, mouse C16N cDNA cloned above was labeled with $^{32}$P, and used as a probe to screen human thalamus cDNA library according to similar procedures to those used in screening for mouse C16N cDNA. Although the clone isolated in this screening was partial one lacking part of its open reading frame, the DNA sequence of this human gene was almost identical to that of mouse gene. We tried therefore to re-clone human DNA sequence containing complete open reading frame by PCR method. Human brain cDNA (CLONTECH) was used as a template in combination with 5'-primer (SEQ ID NO: 11) (5'-ATGATCGATGACACCTACCAGTGC-3') and 3'-primer (5'-CTTCAGGGAAGATGCCTCCT-3' (SEQ ID NO: 12)) prepared on the basis of the mouse sequence. This primer pair will amplify the open reading frame of about 1.8 kb DNA. PCR was conducted following standard procedures, and Taq Extender PCR Additive (STRATAGENE) was added in order to reduce errors in amplification by Taq DNA polymerase. The reaction was conducted under the same conditions as those used in Example 8. As a result, the desired 1.8 kb DNA was obtained almost as a single band. This DNA was subcloned into TA cloning vector, and three of these human DNA clones were selected. The DNA sequence of each clone selected was determined in the usual manner, and their sequences were compared with each other in order to finally determine the base sequence of human C16N cDNA. The base sequence of human C16N cDNA thus determined is shown in SEQ ID NO: 5. The amino acid sequence deduced from the longest open reading frame of the cDNA is shown in SEQ ID NO: 6. It was shown that this human C16N has an extremely high interspecies homology, being different from mouse C16N by only two bases and two amino acids on the base and amino acid levels, respectively.

In addition, variant DNA in which A is substituted for G at position 724 of mouse C16N DNA shown in SEQ ID NO: 3 or in which A is substituted for G at position 489 of human C16N DNA shown in SEQ ID NO: 5 was also obtained in similar procedures to those described above.

Example 11

Activity Measurement of C16N

We studied whether C16N has similar properties to those of C16. In particular, three measurements described in Example 2, i.e., TRAP staining (see 2.3.1), pit formation assay using dentine slice (see 2.3.2) and pit formation assay using Osteologic well (see 2.3.3), were conducted. The measurements were done according to the procedures described in Example 2. The results of the activity measurements which were conducted using C16N expressed by Xenopus oocyte according to similar procedures to those described in Example 2 are as follows. C16N was negative as to TRAP staining. It was also shown that C16N has no pit formation activity in the pit formation assay using dentine slice. On the contrary, C16N gave a satisfactory result in the pit formation assay using Osteologic well; C16N formed an average of 67 pits, which was more than the result of the negative control (in which distilled water instead of cRNA was injected into Xenopus oocyte, and its culture supernatant was added to bone marrow cells) (4 pits on the average), and which was even more than the result of parallel experiment with C16 (41 pits on the average).

Thus, it was shown that C16N has the same properties as those of C16, since it was positive only in the pit formation assay using Osteologic well among the above three assays. Thus, it was found that the differentiated cells induced by C16N were those different from osteoclast and they have hydroxyapatite-resorbing activity. Although experiments for detecting calcitonin receptor were omitted in this Example, the above conclusion that the differentiated cells induced by C16N were not osteoclast is incontrovertible. This is because identification as osteoclast requires all the three requisites, i.e., TRAP stainability, pit formation on dentine slice, and detection of calcitonin receptor, and the differentiated cells induced by C16N have proved in this Example to be negative in two of three requisites.

The following are the results of additional activity measurements on mouse and human C16N expressed from COS-7 cells as described in Example 9, by TRAP staining and the pit formation assay using Osteologic well. Like the above results with oocyte, the result of TRAP staining was negative, and the result of the pit formation assay using Osteologic well was positive. More specifically, mouse and human C16N formed an average of 35 and 15 pits, respectively, whereas the negative control in which the vector alone was introduced into COS-7 cell formed one pit on the average. The expression of C16N by COS-7 cells was thus confirmed.

Example 12

Expression Analysis of C16N Gene by Northern Blotting

According to similar procedures to those described in Example 7, organ-specific expression of C16N gene was analyzed by Northern blotting, and the same expression pattern was obtained as that for C16 obtained in Example 7.

Example 13

Activity of Supporting Survival of Neuron

1) Activity of Supporting Survival of Neuron

PC12D cells were cultured in RPMI 1640 medium supplemented with 5% fetal bovine serum and 5% heat-inactivated horse serum, transferred into serum-free medium, and plated on 24- or 96-well plate at $1–3\times10^5$ cells/ml. Culture supernatant containing C16 or C16N expressed from COS-7 cells was then added. The number of living cells after 72 hours was compared to that observed in the negative control (in which culture supernatant obtained from COS-7 cells transfected with vector alone was added and incubated), and if more than two-fold cells survive, the protein was evaluated as having the activity. As positive control, NGF (Nerve Growth Factor, final concentration 24 ng/ml) was added.

The number of living cells was $4.5\times10^4$ or $6\times10^4$ cells for the supernatant from mouse or human C16N-expressing culture, respectively, whereas the number of living cells in the positive control (NGF) or in the negative control (culture supernatant from the culture transfected with vector alone) was $10.5\times10^4$ or $2\times10^4$ cells, respectively. It was thus shown that mouse and human C16N exhibit the activity of supporting survival of neuron. C16 also gave similar results to those obtained with C16N.

2) Activity of Promoting Adhesion Between Neurons

The activity of C16 and C16N in promoting adhesion between neurons was evaluated according to similar procedures to those described above in Example 13-1. Specifically, PC12D cells were cultured in RPMI 1640 medium supplemented with 5% fetal bovine serum and 5% heat-inactivated horse serum, and plated on 24- or 96-well plate at $1–3\times10^4$ cells/cm$^2$. To the wells, culture supernatant containing C16 or C16N expressed from Xenopus oocyte, and NGF (final concentration of 24 ng/ml) were added. After 72 hours, the number of cell aggregates or clusters comprising more than 10 cells which have elongated nerve fibers was calculated. As a negative control, a similar experiment was conducted by adding NGF and culture supernatant from oocytes containing no factors expressed.

Figure 11:
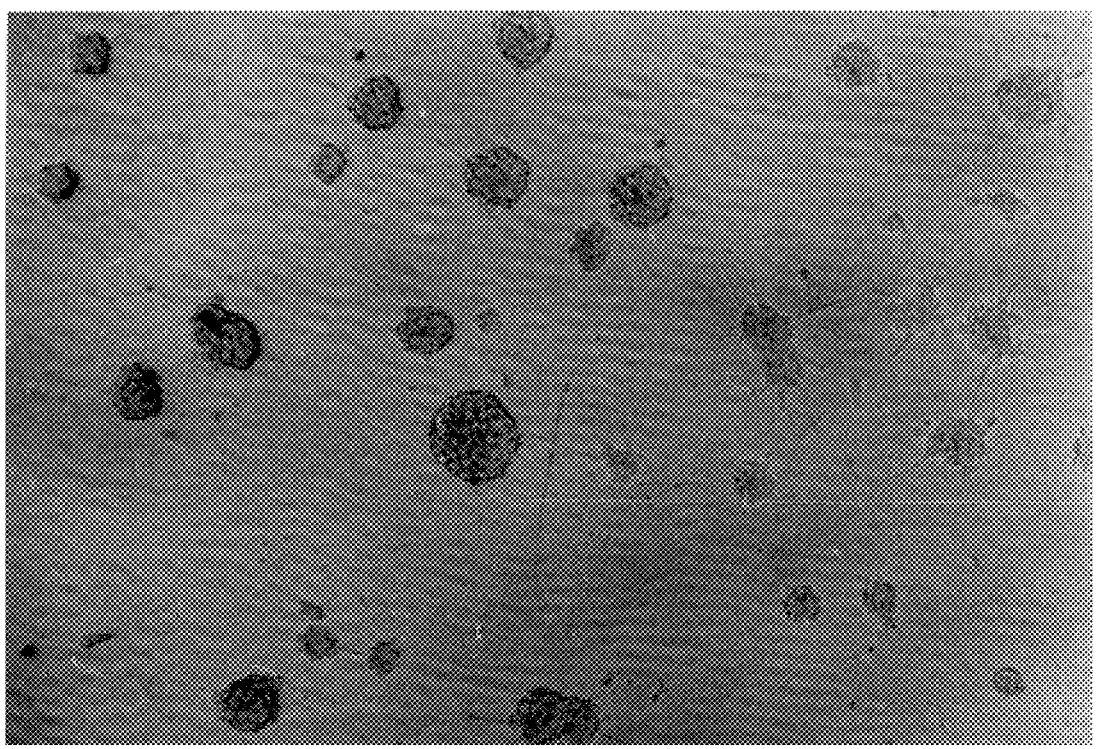
FIG. 11 is microphotograph showing the result of experiments in which cell aggregates or clusters having nerve fibers elongated were observed by adding culture supernatant containing C16N expressed from Xenopus oocytes and NGF to PC12D cells.
Figure 12:
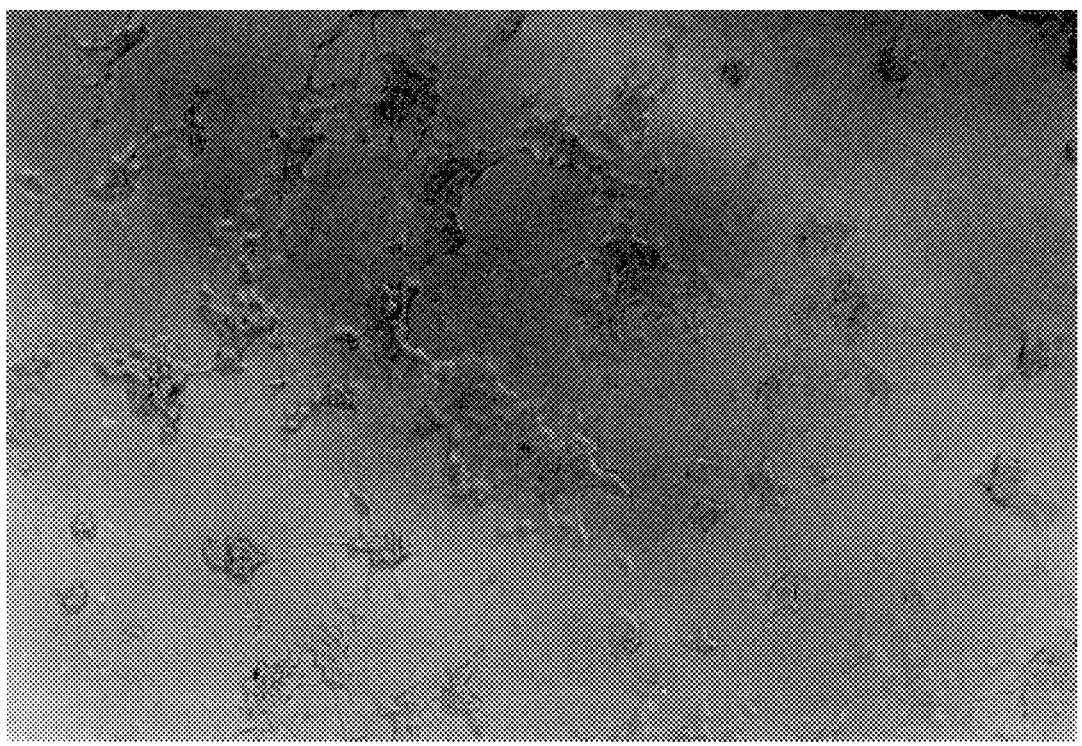
FIG. 12 is microphotograph showing the result of negative control experiment which was conducted in a similar manner to that described for FIG. 11, but in which culture supernatant without the expressed product and NGF were added.

The results for C16N and the negative control were shown in FIGS. 11 or 12, respectively. The number of the aggregates or clusters was 141 for C16N and 121 for C16 which are 3.5- to 4-fold higher than that of the negative control (35). It was thus shown that C16 and C16N have the activity of promoting adhesion between neurons.

In addition, since such activity of promoting adhesion between cells was also observed on NIH 3T3 cells, it is suggested that the factors may have this effect not only on neuron but also on various types of cells.

Example 14

Proliferation Inhibitory Activity on Primary Osteoblast Culture

1) Method for Preparing Primary Osteoblast Culture

From fetal op/op mouse having no osteoclast, cranium was dissected in the form of a disk, and washed with PBS. In 1–2 ml of PBS, four or five craniums were cut into about 1 mm pieces with scissors, suspended in α-MEM medium containing 10% fetal bovine serum, and planted on several dishes. The bone chips were soaked in such an amount of medium that the bone chips did not float. After incubating overnight, flesh medium was added up to the usual volume. The medium of this suspension culture was replaced every 3 days. After several days, cells which crept out of the bone chips and proliferated were subjected to successive cultivation in the 3T3 format (cultivation in which 300,000 cells are subcultured every 3 days). When stained with alkaline phosphatase which is a marker of osteoblast (C. A. G. McCulloch et al., *Blood*, 177, p. 1906 (1991)), almost 100% of these cells was positively stained, although they exhibited divergent stainability. These cells were thus identified as populations of osteoblasts having various differentiation stages.

2) Proliferation Inhibitory Activity

Primary osteoblast culture prepared in 1), at the 2–5 passages, was plated on 96-well plate, and when reached 50% confluent, culture supernatant containing C16N expressed from COS-7 cells as described in Example 9, or culture supernatant from COS-7 cells transfected with vector alone (MOCK) was added to the concentration of 10% with respect to the culture medium. After 18 hours, [$^3$H]-thymidine was added at the final concentration of 0.25 μCi/ml to pulse-label for 4 hours. The cells were washed twice with cold PBS, and then disrupted by adding NaOH and standing the mixture for 30 minutes at room temperature. Cell debris was transferred to a filter using cell harvester, and the radioactivity was measured in liquid scintillation counter.

The amount of incorporated [$^3$H]-thymidine was 580±50 cpm for MOCK supernatant and 480±23 cpm for C16N-containing supernatant. Thus, C16N inhibited incorporation of [$^3$H]-thymidine, and therefore, DNA synthesis by about 20%.

Example 15

Figure 13:
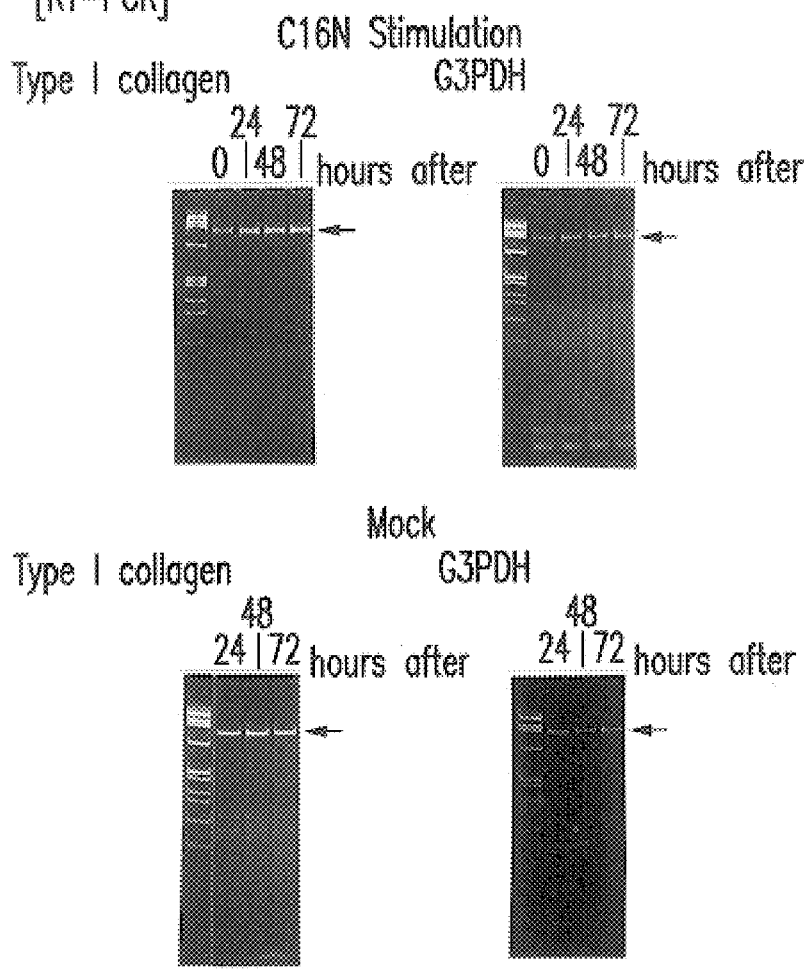
In FIG. 13, panel 1) is electropherogram showing the result of experiments in which total RNA was prepared from primary osteoblast culture to which culture supernatant containing C16N or MOCK culture supernatant had been added, and was subjected to formaldehyde-agarose electrophoresis. One microgram of RNA was applied in each lanes, and stained with ethidium bromide. Panel 2) is electropherogram showing the results of experiments in which mouse gene for type I collagen and control G3PDH gene were amplified by PCR using as templates total RNA prepared from primary osteoblast culture to which culture supernatant containing C16N or mock culture supernatant had been added. One tenth portion of the PCR reaction mixture was applied to each lanes, and stained with ethidium bromide.

Promotion of Expression of Type I Collagen in Primary Osteoblast Culture by C16N 1) Preparation of RNA Primary osteoblast culture prepared in Example 14-1), at the 2–5 passages, was grown to 100% confluent, and further incubated in serum-free medium for two days. Culture supernatant containing C16N expressed from COS-7 cells, or culture supernatant from COS-7 cells transfected with vector alone (MOCK) was added to the concentration of 10% with respect to the culture medium. After 0, 24, 48, and 72 hours, total RNA was prepared from each culture by AGPC method described in Example 1. Each total RNA prepared was subjected to formaldehyde-agarose electrophoresis. The results are shown in FIG. 13-1.

2) Detection of Type I Collagen mRNA by RT-PCR

As primers for amplification of mouse type I collagen gene (C. Genovese et al., *Biochemistry*, 23, p. 6210 (1984)), 5'-primer (SEQ ID NO: 13) (5'-AGCCAGGGTGCCCCCGGTCTTCAGGGAA-3') and 3'-primer (SEQ ID NO: 14) (5'-CTTGGCCCCGGGAGCACCATCCCT-3') were synthesized. The size of DNA fragment amplified with these primers is 941 base pairs. As a control, the G3PDH amplifying primers described in Example 8 were used. The PCR was conducted according to Example 8, except that 19 cycles of amplification were used.

The amount of type I collagen mRNA was increased with time by C16N stimulation. No change in the amount of control G3PDH mRNA was observed. In addition, MOCK did not change the amount of type I collagen mRNA (FIG. 13-2). Type I collagen is the most abundant protein constituting bone matrix, and known as a differentiation marker which is expressed from the early stage during differentiation of osteoblast (*JIKKEN-IGAKU*, vol. 14, No. 10, p. 42 (1996)). Since C16N promotes expression of such type I collagen, and also exhibits inhibitory activity on proliferation of osteoblast as described above in Example 14, it is suggested that C16N may promote differentiation or function of osteoblast.

EFFECTS OF THE INVENTION

The present invention provides novel proteins C16 and C16N, or variant proteins thereof, as well as genes encoding the same. Since these proteins have the activities of inducing cells to become capable of resorbing hydroxyapatite, supporting survival of neuron, inhibiting proliferation of osteoblast, and/or promoting expression of type I collagen in osteoblast, it is expected that they may be useful as therapeutic agents for a wide variety of diseases which can be treated with these functions.

What is claimed is:

1. An isolated DNA selected from the group consisting of:
   (a) a DNA comprising the contiguous base sequence of SEQ ID NO:1;
   (b) a DNA encoding a protein comprising the contiguous amino acid sequence of SEQ ID NO:2;
   (c) a DNA comprising the contiguous base sequence of SEQ ID NO:3 or 5; and
   (d) a DNA encoding a protein comprising the contiguous amino acid sequence of SEQ ID NO:4 or 6.

2. An isolated DNA comprising a polynucleotide that hybridizes to a DNA consisting of the contiguous base sequence of SEQ ID NO: 1, 3 or 5, under conditions of an aqueous solution of 50% formamide, 5× SSC, 1× Denhardt's solution, 25 mM NaPO$_4$, pH 6.8, 50 µg/ml salmon sperm DNA at 42° C., wherein said isolated DNA encodes a protein having all of the following properties (1), (2), (3) and (4):

(1) activity of inducing cells to become capable of resorbing hydroxyapatite;
   (2) activity of supporting survival of neurons;
   (3) activity of inhibiting proliferation of osteoblasts;
   (4) activity of promoting expression of type I collagen in osteoblasts.

3. An expression vector containing the DNA of claim 1 or 2.

4. A host cell containing the expression vector of claim 3.

5. A process for producing a recombinant protein, comprising culturing the host cell of claim 4 under conditions in which the expression vector can be expressed and recovering the recombinant protein.

* * * * *